US012622934B2

(12) United States Patent
Seo et al.

(10) Patent No.: US 12,622,934 B2
(45) Date of Patent: *May 12, 2026

(54) PHARMACEUTICAL COMPOSITION FOR PREVENTING OR TREATING ATOPIC DISEASE CONTAINING *Faecalibacterium prausnitzii* STRAIN

(71) Applicant: ENTEROBIOME INC., Goyang-si (KR)

(72) Inventors: Jae-Gu Seo, Gimpo-si (KR); Joo-Hyun Shin, Seoul (KR); Dokyung Lee, Seoul (KR); Yoonmi Lee, Seoul (KR); Seo Yul Jang, Goyang-si (KR); Hye Rim Byeon, Paju-si (KR)

(73) Assignee: ENTEROBIOME INC., Goyang-si (KR)

( * ) Notice: Subject to any disclaimer, the term of this patent is extended or adjusted under 35 U.S.C. 154(b) by 537 days.

This patent is subject to a terminal disclaimer.

(21) Appl. No.: 18/017,307

(22) PCT Filed: Feb. 26, 2021

(86) PCT No.: PCT/KR2021/002433
§ 371 (c)(1),
(2) Date: Jan. 20, 2023

(87) PCT Pub. No.: WO2022/045502
PCT Pub. Date: Mar. 3, 2022

(65) Prior Publication Data
US 2023/0372408 A1    Nov. 23, 2023

(30) Foreign Application Priority Data

Aug. 26, 2020    (KR) ........................ 10-2020-0107619

(51) Int. Cl.
*A61K 35/74*        (2015.01)
*A23L 33/135*       (2016.01)
*A61K 45/06*        (2006.01)
*A61P 37/08*        (2006.01)

(52) U.S. Cl.
CPC ........... *A61K 35/74* (2013.01); *A23L 33/135* (2016.08); *A61K 45/06* (2013.01); *A61P 37/08* (2018.01)

(58) Field of Classification Search
None
See application file for complete search history.

(56) References Cited

U.S. PATENT DOCUMENTS

| | | | |
|---|---|---|---|
| 2018/0085429 A1 | 3/2018 | Langella et al. | |
| 2018/0264053 A1 | 9/2018 | Lynch et al. | |
| 2018/0333440 A1 | 11/2018 | Finlay et al. | |

FOREIGN PATENT DOCUMENTS

| | | |
|---|---|---|
| KR | 10-2013-0034764 A | 4/2013 |
| KR | 10-2016-0053447 A | 5/2016 |
| KR | 10-2016-0069733 A | 6/2016 |
| KR | 10-1667496 B1 | 10/2016 |
| KR | 10-2018-0070342 A | 6/2018 |
| KR | 10-1925135 B1 | 12/2018 |
| KR | 10-2185828 B1 | 11/2020 |
| WO | 2016/075294 A1 | 5/2016 |

OTHER PUBLICATIONS

Marco Candela, et al. "Unbalance of intestinal microbiota in atopic children", BMC Microbiology, 2012, pp. 1-9, vol. 12, article 95.
International Search Report for PCT/KR2021/002433 dated Jun. 2, 2021 [PCT/ISA/210].
Written Opinion for PCT/KR2021/002433 dated Jun. 2, 2021 [PCT/ISA/237].
Han SONG, PhD, et al., "*Faecalibacterium prausnitzii* subspecies-level dysbiosis in the human gut microbiome underlying atopic dermatitis", J Allergy Clin Immunol., Oct. 2015, vol. 137, No. 3, pp. 852-860 (9 pages total).
Extended European Search Reported issued Jan. 5, 2024 in European Application No. 21861805.6.

*Primary Examiner* — Brian Gangle
(74) *Attorney, Agent, or Firm* — Sughrue Mion, PLLC

(57) ABSTRACT

A pharmaceutical composition effective for the prevention or treatment of atopic disease is disclosed. The pharmaceutical composition contains a *Faecalibacterium prausnitzii* EB-FPDK11 strain or a culture or dried product thereof. While traditional probiotics generally have an insignificant therapeutic effect for atopic disease, the pharmaceutical composition of the present invention exhibits a preventive or therapeutic effect on atopic disease at the same level as that of steroid-based drugs, and thus is not only promising as pharmabiotics, but also useful in the development of food and cosmetics.

16 Claims, 14 Drawing Sheets

Specification includes a Sequence Listing.

A : *Faecalibacterium prausnitzii* A2-165          B : *Faecalibacterium prausnitzii* EB-FPDK11

| ATCC 19615 | A2-165 | FPHS1 |
|---|---|---|
|  |  |  |

FIG. 15

SEQUENCE LISTING

<160> NUMBER OF SEQ ID NOS: 8

<210> SEQ ID NO 1
<211> LENGTH: 1433
<212> TYPE: DNA
<213> ORGANISM: Faecalibacterium prausnitzii

<400> SEQUENCE: 1

```
gacgaacgct ggcggcgcgc ctaacacatg caagtcgaac gagcgagaga gagcttgctt      60
tctcgagcga gtggcgaacg ggtgagtaac gcgtgaggaa cctgcctcaa agaggggggac     120 aacagttgga aacgactgct aataccgcat aagcccacag gtcggcatcg accagaggga     180
aaaggagcaa tccgctttga gatggcctcg cgtccgatta gctagttggt gaggtaacgg     240
cccaccaagg caacgatcgg tagccggact gagaggttga acggccacat tgggactgag     300
acacggccca gactcctacg ggaggcagca gtggggaata ttgcacaatg ggggaaaccc     360
tgatgcagcg acgccgcgtg gaggaagaag gtcttcggat tgtaaactcc tgttgttgag     420
gaagataatg acggtactca acaaggaagt gacggctaac tacgtgccag cagccgcggt     480
aaaacgtagg tcacaagcgt tgtccggaat tactgggtgt aaagggagcg caggcgggaa     540
gacaagttgg aagtgaaatc tatgggctca acccataaac tgctttcaaa actgtttttc     600
ttgagtagtg cagaggtagg cggaattccc ggtgtagcgg tggaatgcgt agatatcggg     660
aggaacacca gtggcgaagg cggcctactg ggcaccaact gacgctgagg ctcgaaagtg     720
tgggtagcaa acaggattag ataccctggt agtccacacc gtaaacgatg attactaggt     780
gttggaggat tgacccccttc agtgccgcag ttaacacaat aagtaatcca cctggggagt     840
acgaccgcaa ggttgaaact caaaggaatt gacgggggcc cgcacaagca gtggagtatg     900
tggtttaatt cgacgcaacg cgaagaacct taccaagtct tgacatccct tgacgaacat     960
agaaatgtgt tttctcttcg gagcaaggag acaggtggtg catggttgtc gtcagctcgt    1020
gtcgtgagat gttgggttaa gtcccgcaac gagcgcaacc cttactgtca gttactacgc    1080
aagaggactc tggcaggact gccgttgaca aaacggagga aggtggggat gacgtcaaat    1140
catcatgccc tttatgactt gggctacaca cgtactacaa tggcgttaaa caaagagaag    1200
caagaccgcg aggtggagca aaactcagaa acaacgtccc agttcggact gcaggctgca    1260
actcgcctgc acgaagtcgg aattgctagt aatcgtggat cagcatgcca cggtgaatac    1320
gttcccgggc cttgtacaca ccgcccgtca caccatgaga gccggggggga cccgaagtcg    1380 gtagtctaac cgcaaggagg acgccgccga aggtaaaact ggtgattggg gtg           1433
```

<210> SEQ ID NO 2
<211> LENGTH: 17
<212> TYPE: DNA
<213> ORGANISM: Artificial Sequence
<220> FEATURE:
<223> OTHER INFORMATION: FP1 primer forward

<400> SEQUENCE: 2

```
actcaacaag gaagtga                                                     17
```

-continued

```
<210> SEQ ID NO 3
<211> LENGTH: 17
<212> TYPE: DNA
<213> ORGANISM: Artificial Sequence
<220> FEATURE:
<223> OTHER INFORMATION: FP2 primer reverse

<400> SEQUENCE: 3
cagaggtagg cggaatt                                                        17

<210> SEQ ID NO 4
<211> LENGTH: 22
<212> TYPE: DNA
<213> ORGANISM: Artificial Sequence
<220> FEATURE:
<223> OTHER INFORMATION: ERIC-1 primer forward

<400> SEQUENCE: 4
atgtaagctc ctggggattc ac                                                  22

<210> SEQ ID NO 5
<211> LENGTH: 22
<212> TYPE: DNA
<213> ORGANISM: Artificial Sequence
<220> FEATURE:
<223> OTHER INFORMATION: ERIC-2 primer reverse

<400> SEQUENCE: 5
aagtaagtga ctggggtgag cg                                                  22

<210> SEQ ID NO 6
<211> LENGTH: 15
<212> TYPE: DNA
<213> ORGANISM: Artificial Sequence
<220> FEATURE:
<223> OTHER INFORMATION: (GTG)5 primer forward/reverse

<400> SEQUENCE: 6
gtggtggtgg tggtg                                                          15

<210> SEQ ID NO 7
<211> LENGTH: 20
<212> TYPE: DNA
<213> ORGANISM: Artificial Sequence
<220> FEATURE:
<223> OTHER INFORMATION: 27F primer forward

<400> SEQUENCE: 7
agagtttgat cmtggctcag                                                     20

<210> SEQ ID NO 8
<211> LENGTH: 19
<212> TYPE: DNA
<213> ORGANISM: Artificial Sequence
<220> FEATURE:
<223> OTHER INFORMATION: 1492R primer reverse

<400> SEQUENCE: 8
ggttaccttg ttacgactt                                                      19
```

PHARMACEUTICAL COMPOSITION FOR PREVENTING OR TREATING ATOPIC DISEASE CONTAINING *Faecalibacterium prausnitzii* STRAIN

CROSS REFERENCE TO RELATED APPLICATIONS

This application is a National Stage of International Application No. PCT/KR2021/002433 filed Feb. 26, 2021, claiming priority based on Korea Patent Application No. 10-2020-0107619 filed Aug. 26, 2020.

INCORPORATION BY REFERENCE OF SEQUENCE LISTING

The content of the electronically submitted sequence listing, file name: Q284319_Sequence_Listing_As_Filed.txt; size: 3,647 bytes; and date of creation: Jan. 20, 2023, filed herewith, is incorporated herein by reference in its entirety.

TECHNICAL FIELD

The present invention relates to a pharmaceutical composition for preventing or treating atopic disease, and more particularly to a pharmaceutical composition for preventing or treating atopic disease containing a *Faecalibacterium prausnitzii* EB-FPDK11 strain as an active ingredient.

BACKGROUND ART

In a strict sense, the term "atopy" refers to a predisposition to abnormally produce IgE in response to foreign substances entering the body from the outside. Thus, the team "atopy" is not the same as the team "allergy", but these two terms are used interchangeably with substantially the same meaning. The clinical manifestations of such hypersensitivity are referred to as "atopic diseases" or "allergic diseases". Traditionally, asthma, allergic rhinitis, allergic conjunctivitis, atopic dermatitis, urticaria, anaphylaxis, and food allergy and the like are classified as atopic diseases.

Although the causes of atopic diseases known to date are not accurately identified, it is generally believed that genetic and immunological factors are involved in atopic diseases, and it is a common opinion of experts that other environmental and mental factors act to exacerbate atopic diseases. It is known that atopic diseases are not single diseases, but are multiple diseases, including atopic dermatitis, asthma and allergic rhinitis, which occur with atomic march or appear simultaneously.

Among atopic diseases, atopic dermatitis is a chronic recurrent skin disease that affects newborns or children as well known to the public and may persist until adulthood. As the main symptom of atopic dermatitis, erythematous papules and blisters with severe itching occur in the acute phase, which is the initial stage of the disease, and they progress to exudative lesions that ooze when scratched, and at this time, secondary infections often occur. As the lesions progress, excoriations and papules occur in the subacute phase, and when the chronic phase is reached, lichenification occurs in which the skin becomes thickened. Atopic patients may receive repeated emergency care and hospitalization due to frequent recurrence and worsening symptoms, and have difficulty in normal school life, social life, or work life, resulting in mental pain, which may make normal life difficult.

Since it is difficult to fundamentally cure atopic diseases and the symptoms thereof tend to be severe, symptoms of atopic diseases are controlled through appropriate treatment without aiming to cure the atopic diseases. Currently, atopic dermatitis is mainly treated by drug therapy such as steroids, antihistamines and antibiotics. The currently most widely used therapeutic agent is dexamethasone known as a steroidal drug. Steroidal drugs have excellent anti-inflammatory and immunosuppressive effects, but when they are used for a long period of time, a problem arises in that side effects such as skin weakness, systemic hormonal symptoms, and addictive symptoms occur. Antihistamines reduce itching symptoms by inhibiting the release of histamine from mast cells, but are used as a temporary measure and may cause side effects such as insomnia, anxiety and loss of appetite for a long time.

As described above, synthetic drugs have severe side effects when used for a long period of time, and thus new treatments for atopy that have no side effects while being effective against atopic diseases are needed. As new treatments for atopy without side effects, new microbial drugs are attracting attention. Accordingly, the efficacy and function of probiotics are also attracting great attention. However, how microorganisms work in the body remains a considerable challenge, and in terms of efficacy, microorganisms merely help to keep the intestinal environment healthy, and hardly appear to exhibit certain pharmaceutical efficacy. Therefore, there is an urgent need to develop next-generation pharmabiotic treatments that have proven pharmaceutical efficacy for atopic diseases which are intractable diseases.

PRIOR ART DOCUMENTS

Patent Documents (Patent Document 1) KR20160069733 A
(Patent Document 2) KR20130034764 A
(Patent Document 3) KR101925135 B

DISCLOSURE

Technical Problem

The present invention has been conceived to overcome the above-described problems, and an object of the present invention is to provide a pharmaceutical composition for preventing or treating atopic disease containing a *Faecalibacterium prausnitzii* strain (KCCM12621P) as an active ingredient.

Specifically, an object of the present invention is to provide a pharmaceutical composition for preventing or treating atopic disease, the pharmaceutical composition containing a *Faecalibacterium prausnitzii* EB-FPDK11 strain which is excellent in suppressing excessive secretion of the immune hypersensitivity mediator IgE and achieving a balanced regulation between Th1-type cytokine and Th2-type cytokine immune responses.

Another object of the present invention is to provide a health functional food for preventing or ameliorating atopic disease containing a *Faecalibacterium prausnitzii* EB-FPDK11 strain (KCCM12621P) as an active ingredient.

Still another object of the present invention is to provide a cosmetic composition for alleviating or ameliorating atopic disease containing a *Faecalibacterium prausnitzii* EB-FPDK11 strain (KCCM12621P) as an active ingredient.

Technical Solution

One aspect of the present invention is directed to a pharmaceutical composition for preventing or treating atopic disease, the pharmaceutical composition containing a *Faecalibacterium prausnitzii* EB-FPDK11 strain (accession number: KCCM12621P) or a culture or dried product of the strain.

Another aspect of the present invention is directed to a food for preventing or ameliorating atopic disease, the food containing a *Faecalibacterium prausnitzii* EB-FPDK11 strain (KCCM12621P) or a culture or dried product of the strain.

Still another aspect of the present invention is directed to a cosmetic composition for alleviating or ameliorating atopic disease, the cosmetic composition containing a *Faecalibacterium prausnitzii* EB-FPDK11 strain (KCCM12621P) or a culture or dried product of the strain.

Advantageous Effects

The pharmaceutical composition for preventing or treating atopic disease containing the *Faecalibacterium prausnitzii* EB-FPDK11 strain as an active ingredient according to the present invention has an excellent effect of treating atopic disease, and exhibits the effect of preventing, ameliorating or treating atopic dermatitis at the same level as that of a steroidal drug.

In addition, the pharmaceutical composition for preventing or treating atopic disease containing the *Faecalibacterium prausnitzii* EB-FPDK11 strain as an active ingredient according to the present invention is excellent in achieving a balanced regulation between Th1 and Th2 cell immune responses, and especially achieves a balanced regulation between Th1 type cytokine and Th2 type cytokine immune responses through different immunoregulatory mechanisms depending on the severity of atopic dermatitis.

In addition, the pharmaceutical composition of the present invention directly reduces the level of serum immunoglobulin IgE, which is a major factor in the onset of atopic disease, and reduces the infiltration of mast cells, eosinophils and neutrophils into dermal cells. Thus, the pharmaceutical composition may be applied to a pharmaceutical composition for preventing or treating atopic disease, a health functional food, a cosmetic composition, and the like.

DESCRIPTION OF DRAWINGS

The above and other objects, features, and advantages of the present invention will be more clearly understood from the following detailed description taken in conjunction with the accompanying drawings, in which:

FIGS. 15A and 15B show hematoxylin and eosin stained dorsal tissue of mice treated with PBS or the *Faecalibacterium prausnitzii* EB-FPDK11 strain of the present invention;

MODE FOR INVENTION

Figure 1:
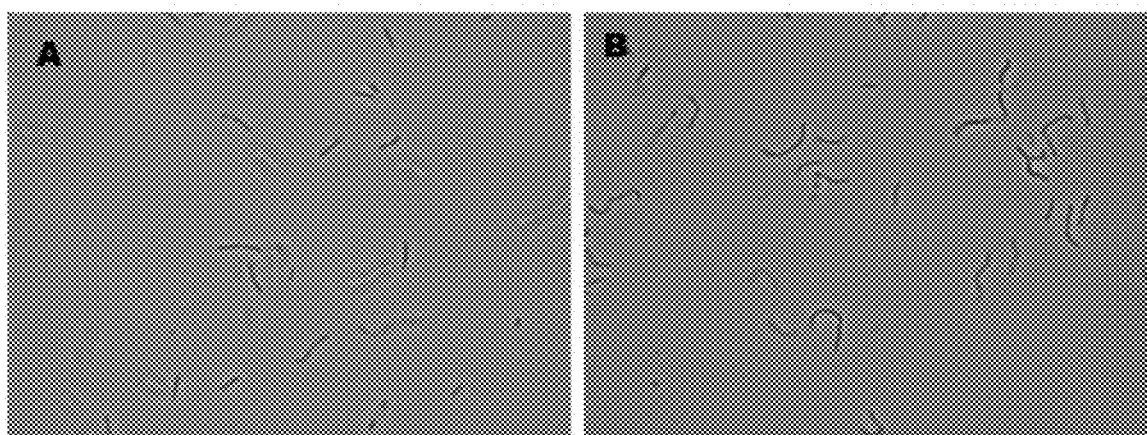
FIG. 1 shows the results of microscopic observation of the *Faecalibacterium prausnitzii* EB-FPDK11 strain of the present invention and a *Faecalibacterium prausnitzii* A2-165 strain which is a type strain.

Hereinafter, the present invention will be described in more detail with reference to the accompanying drawings.

Unless otherwise defined, all technical and scientific terms used herein have the same meanings as commonly understood by those skilled in the art to which the present invention pertains.

As used herein, the term "about", when used in reference to a particular recited numerical value, means that the value may vary from the recited value by no more than 1%. For example, as used herein, the expression "about 100" includes 99 and 101 and all values in between (e.g., 99.1, 99.2, 99.3, 99.4, etc.).

Throughout the present specification, it is to be understood that when any part is referred to as "including" any component, it does not exclude other components, but may further include other components, unless otherwise specified.

As used herein, the term "atopic allergy" refers to a disease causing allergic reactions, and is meant to include asthma, atopic dermatitis, allergic rhinitis (hay fever), urticaria, anaphylaxis, angioedema, food allergy, etc.

As used herein, the term "preventing" refers to any action that suppresses or delays the onset of atopic disease by administration of the pharmaceutical composition according to the present invention.

As used herein, the terms "treat", "treating", or the like mean to alleviate symptoms, eliminate the causation of symptoms either on a temporary or permanent basis, or to prevent or slow the appearance of symptoms of the named disorder or condition.

As used herein, the term "ameliorating" refers to any action that reduces a parameter associated with an abnormal condition, for example, the severity of symptoms.

As used herein, the term "pharmaceutically acceptable" refers to compositions which are, within the scope of sound medical judgment, suitable for use in contact with the tissues of subjects (e.g., human beings) without excessive toxicity, irritation, allergic response, or other problem or complication, commensurate with a reasonable benefit/risk ratio.

Pharmabiotics are defined as bacterial cells of human origin, or their products, with a proven pharmacological role in health or disease ("Probiotics and pharmabiotics," Bioeng Bugs. 2010 March-April; 1(2): 79-84). One aspect of the present invention is directed to a pharmaceutical composition for preventing or treating atopic disease containing a *Faecalibacterium prausnitzii* EB-FPDK11 strain (accession number: KCCM12621P) as an active ingredient and being usable as a pharmabiotic.

The *Faecalibacterium prausnitzii* EB-FPDK11 strain (accession number: KCCM12621P) of the present invention has the 16s rRNA gene of SEQ ID NO: 1.

The *Faecalibacterium prausnitzii* EB-FPDK11 strain that is used in the present invention is a mucin-degrading bacterium isolated from the feces of healthy Koreans, is rod-shaped, is anaerobic, is not motile, is gram-negative, and does not form endospores. The *Faecalibacterium prausnitzii* EB-FPDK11 strain may use mucus as the sole source of carbon and nitrogen by producing several mucolytic enzymes, may metabolize various carbon sources, including glucose, galactose, N-acetylglucosamine and lactose, and produce, as major metabolites, short-chain fatty acids such as propionic acid and acetic acid.

IgE, which is produced in response to allergen challenge triggers potent agonist mechanisms associated with atopic disease. When bound to high affinity receptors on mast cells and basophils, IgE can be cross-linked by allergen, leading to degranulation and the release of histamine, leukotrienes, and other inflammatory mediators. These agents directly mediate the symptoms of wheezing, bronchoconstriction, and rhinitis associated with early and late phase allergic reactions, while cytokines and chemokines released by mast cells and basophils contribute to local inflammatory reactions. Thus, neutralization of IgE can be an effective treatment strategy for the treatment of atopic diseases.

The *Faecalibacterium prausnitzii* EB-FPDK11 strain of the present invention produces short-chain fatty acids (SCFAs) such as butyrate, acetate and propionate through anaerobic fermentation of carbohydrates. SCFA receptors are expressed in macrophages, dendritic cells and neutrophils, and can modulate T and B cell mediated responses. SCFAs also play an important role in the production and modulation of regulatory T (Treg) cells. Butyrate induces extrathymic differentiation of regulatory T (Treg) cells, and propionate potentiates the production of Tregs in the periphery. SCFAs can also regulate T cell differentiation into Th17, Th1 and IL-10-producing T cells by their histone deacetylase inhibitor activity.

In atopic dermatitis patients, expression of low-affinity IgE receptors in B cells and monocytes increases, IL-4 secretion from peripheral blood monocytes increases, and interferon-gamma secretion decreases, resulting in an increase in IgE production. In atopic patients, among the subgroups of T helper cells, Th2 cells that mainly secrete IL-4 and IL-5 are increase, and Th1 cells that secrete IL-2 and INF-γ relatively decrease. IL-4 induces differentiation into IgE during immunoglobulin production, and activates adhesion molecules to help inflammatory cells such as monocytes and eosinophils to move to inflamed tissue cells. IL-5 prolongs the survival of eosinophils and promotes histamine secretion from basophils. In allergic diseases, selective target memory Th2 cells exist, causing lesions in selective target organs.

The pharmaceutical composition for preventing or treating atopic disease according to the present invention functions to achieve Th1/Th2 balance in a situation where Th2 is dominant. Therefore, the pharmaceutical composition is effective for preventing or treating atopic dermatitis, asthma, and rhinitis, which are caused by Th1/Th2 imbalance due to an excessive Th2 response. It is generally known that changes in cytokine levels in atopic dermatitis are caused by an immune system based on Th2 activation in which differentiation of undifferentiated T-helper cells 1 (Th1) to T-helper cells 2 (Th2) is highly promoted. In this Th2 cell activation process, Th2 cells produce IL-4, IL-5, IL-6, IL-13, IL-9 and IL-10.

The *Faecalibacterium prausnitzii* EB-FPDK11 strains are live or pasteurized. For use, the *Faecalibacterium prausnitzii* EB-FPDK11 strain of the invention may be cultured, recovered by a separation process such as centrifugation, and dried, for example, freeze-dried to form a probiotic. Pasteurization of the *Faecalibacterium prausnitzii* EB-FPDK11 strain means heating the strain at a temperature of 50° C. to 100° C. for 10 minutes or more. For example, the strain may be pasteurized at 70° C. for 30 minutes.

The pharmaceutical composition of the present invention may contain, as an active ingredient, the *Faecalibacterium*

*prausnitzii* EB-FPDK11 strain in an amount of $10^8$ to $10^{12}$ live bacteria (CFU), or contain a culture product having the same CFU of live bacteria.

In one embodiment of the present invention, for use, the pharmaceutical composition containing the *Faecalibacterium prausnitzii* EB-FPDK11 strain may be formulated in oral dosage forms, including powders, granules, tablets, capsules, suspensions, emulsions, syrup and aerosol, preparations for external application, suppositories, and sterile injectable solutions, according to respective conventional methods, but is not necessarily limited thereto.

The pharmaceutical composition of the present invention may be formulated as a product for intestinal or oral administration. In addition, the pharmaceutical composition of the present invention may be prepared in the form of an enteric coated preparation in order for the composition to pass through the stomach and reach the small intestine safely and to release the active ingredient microorganism therein quickly, according to a known method.

In one embodiment of the present invention, liquid formulations for oral administration include suspensions, solutions, emulsions and syrup, and may contain, but are not necessarily limited to, various excipients, for example, wetting agents, sweetening agents, flavoring agents and preservatives, in addition to water and liquid paraffin, which are frequently used simple diluents.

In other embodiments, the pharmaceutical composition for preventing or treating atopic diseases according to the present invention may further contain at least one vitamin. The at least one vitamin may be fat-soluble or water-soluble vitamins. Suitable vitamins include, but are not necessarily limited to, vitamin D, vitamin C, vitamin A, vitamin E, vitamin B12, vitamin K, riboflavin, niacin, vitamin B6, folic acid, pyridoxine, thiamine, pantothenic acid, and biotin. Suitable forms of any of the foregoing are salts of the vitamin, derivatives of the vitamin, compounds having the same or similar activity of the vitamin, and metabolites of the vitamin.

The pharmaceutical composition for preventing or treating atopic disease according to the present invention may further contain a known additional therapeutic agent having an effect of preventing and treating allergic disease or atopic dermatitis. Additional therapeutic agents that may be used in the present invention are immunosuppressants, analgesics, steroids, non-steroidal anti-inflammatory agents (NSAIDs) or cytokine antagonists, and combinations thereof. Examples of the immunosuppressants include, but are not necessarily limited to, calcineurin inhibitors including glucocorticoid, cyclosporine, tacrolimus (FK506), pimecrolimus, and ISA(TX)247, rapamycin, a Type IV PDE inhibitor, mycophenolate mofetil, dexamethasone, and the like. For example, all kinds of known immunosuppressants may be used herein. In addition, one immunosuppressant may be used alone, or two or more immunosuppressants may be used in combination. Preferably, at least one selected from the group consisting of cyclosporine, tacrolimus, dexamethasone, and pimecrolimus may be used as the immunosuppressant. Where the pharmaceutical composition according to the present invention is used in combination with a second therapeutic agent, it may be administered sequentially or simultaneously with the second therapeutic agent, and may be administered alone or several times.

The pharmaceutical composition of the present invention may further contain a pharmaceutically acceptable carrier and/or excipient in addition to the active ingredient, and may be formulated with various additives which are commonly in the pharmaceutical field, such as binders, disintegrants, coating agents, and lubricants.

Excipients that may be used in the present invention include saccharides such as sucrose, lactose, mannitol and glucose, and starches such as corn starch, potato starch, rice starch, and partially pregelatinized starch. Binders include polysaccharides such as dextrin, sodium alginate, carrageenan, guar gum, acacia gum and agar; naturally-occurring macromolecular substances such as tragacanth, gelatin, and gluten; cellulose derivatives such as hydroxypropylcellulose, methylcellulose, hydroxypropylmethyl cellulose, ethylcellulose, hydroxypropylethylcellulose, and carboxymethylcellulose sodium; and polymers such as polyvinylpyrrolidone, polyvinyl alcohol, polyvinyl acetate, polyethylene glycol, polyacrylic acid, polymethacrylic acid, and vinyl acetate resin.

Examples of disintegrants that may be used in the present invention include cellulose derivatives such as carboxymethylcellulose, calcium carboxymethylcellulose, and low-substituted hydroxypropylcellulose; and starches such as sodium carboxymethyl starch, hydroxypropyl starch, corn starch, potato starch, rice starch, and partially pregelatinized starch.

Examples of lubricants that may be usable in the present invention include talc, stearic acid, calcium stearate, magnesium stearate, colloidal silica, hydrous silicon dioxide, and various types of waxes and hydrogenated oils.

Coating agents include, but are not necessarily limited to, water-insoluble polymers such as dimethylaminoethyl methacrylate-methacrylic acid copolymers, polyvinylacetaldiethylaminoacetate, ethylacrylate-methacrylic acid copolymers, ethylacrylate-methylmethacrylate-chlorotrimethyl ammonium ethylmethacrylate copolymers, and ethylcellulose; enteric polymers such as methacrylic acid-ethyl acrylate copolymers, hydroxypropylmethyl cellulose phthalate, and hydroxypropylmethyl cellulose acetate succinate; and water-soluble polymers such as methylcellulose, hydroxypropylmethylcellulose, polyvinylpyrrolidone, and polyethylene glycol.

The dosage of the strain as an active ingredient in the pharmaceutical composition for preventing or treating atopic disease according to the present invention may be determined depending on factors, including various types of diseases, the patients' age, body weight, sex and medical condition, severity of the condition, sensitivity to a drug, the time of administration, the route of administration, the rate of excretion, the duration of treatment, and drugs used in combination with the composition, as well as other factors well known in the medical field. Thus, the dosage regimen may vary widely, but it is important to administer a minimal amount that can achieve the maximum effect without side effects taking into consideration all of the above factors, and this dosage regimen may be determined routinely by a person skilled in the art using standard methods.

Generally, for adults, $1 \times 10^8$ or more live or pasteurized bacteria, preferably $1 \times 10^8$ to $1 \times 10^{12}$ live or pasteurized bacteria, may be taken once or several times as needed. In one embodiment of the present invention, the content of the *Faecalibacterium prausnitzii* EB-FPDK11 strain in the pharmaceutical composition for preventing or treating atopic disease is not particularly limited as long as the pharmaceutical composition contains the strain. However, the pharmaceutical composition may contain the *Faecalibacterium prausnitzii* EB-FPDK11 strain at a concentration of $1 \times 10^8$ cells/ml to $1 \times 10^{10}$ cells/ml, but the concentration is not necessarily limited thereto. For example, the concentration of the *Faecalibacterium prausnitzii* EB-FPDK11 strain in the pharmaceutical composition may be $1 \times 10^8$ cells/ml to $1 \times 10^{10}$ cells/ml, $2 \times 10^8$ cells/ml to $1 \times 10^{10}$ cells/ml, $3 \times 10^8$ cells/ml to $1 \times 10^{10}$ cells/ml, $5 \times 10^8$ cells/ml to $1 \times 10^{10}$ cells/ml, $1 \times 10^8$ cells/ml to $5 \times 10^9$ cells/ml, $2 \times 10^8$ cells/ml to $5 \times 10^9$ cells/ml, $3 \times 10^8$ cells/ml to $5 \times 10^9$ cells/ml, or $5 \times 10^8$ cells/ml to $5 \times 10^9$ cells/ml, but is not necessarily limited thereto.

Another aspect of the present invention is directed to a food or health functional food containing the *Faecalibacterium prausnitzii* EB-FPDK11 strain or a culture or dried product thereof.

The food containing the strain according to the present invention may be taken as various foods or nutritional products such as milk or dairy products, or taken as food supplements or health functional foods. According to one embodiment of the present invention, examples of the products include, but are not necessarily limited to, foods such as dairy products, beverages, juices, soups, or children's foods.

Still another aspect of the present invention is directed to a cosmetic composition for alleviating or ameliorating atopic dermatitis containing the *Faecalibacterium prausnitzii* EB-FPDK11 strain or a culture or dried product thereof.

The cosmetic composition of the present invention may contain ingredients that are commonly used in cosmetic compositions, in addition to the above active ingredient, and may contain conventional adjuvants such as antioxidants, stabilizers, solubilizers, vitamins, colorants and flavoring agents, and carriers.

The cosmetic composition may be characterized by having a function of ameliorating one or more skin conditions selected from the group consisting of skin allergies, skin urticaria, atopic dermatitis, psoriasis, fungal infections, and eczema, but the function is not necessarily limited to amelioration of these skin conditions.

The cosmetic composition of the present invention may be formulated in any conventional form known in the art. For example, the cosmetic composition may be formulated in the form of solution, suspension, emulsion, paste, gel, cream, lotion, powder, soap, surfactant-containing cleansing, oil, powder foundation, emulsion foundation, wax foundation, pack, mask pack, massage cream, and spray. More specifically, the cosmetic composition may be formulated in the form of skin softener, lotion, nourishing cream, massage cream, essence, eye cream, cleansing cream, cleansing foam, cleansing water, spray or powder.

Hereinafter, the present invention will be described with reference to examples. It is to be understood, however, that the following examples serve merely to illustrate the present invention, and the scope of the present invention is not limited by the following examples

EXAMPLES

Examples 1: Isolation and Identification of *Faecalibacterium prausnitzii* EB-FPDK11 Strain

1.1. Isolation and Identification of Strain

To isolate *Faecalibacterium prausnitzii* from feces of healthy Koreans (female, 9 years old, BMI 15.5), culture was performed using YBHI medium (brain heart infusion medium supplemented with 0.5% yeast extract, 0.1% D-cellobiose and 0.1% D-maltose) (Difco, Detroit, USA) in an anaerobic chamber under stringent oxygen-free conditions (5% $H_2$, 15% $CO_2$ and 80% $N_2$) according to the method of Martin, and then an EOS (Extremely Oxygen Sensitivity) strain was selected and isolated.

1.2. Microscopic Observation

In order to confirm whether the isolated strain was a *Faecalibacterium prausnitzii* strain, the isolated strain was observed under a microscope. As shown in FIG. 1, as a result of observing the type strain *Faecalibacterium prausnitzii* A2-165 strain (A) and the *Faecalibacterium prausnitzii* EB-FPDK11 strain (B) at 1,000× magnification, it was confirmed that the shapes of the strains were all straight or curved rod-shaped cells and were similar to each other.

1.3. PCR Analysis

Figure 2:
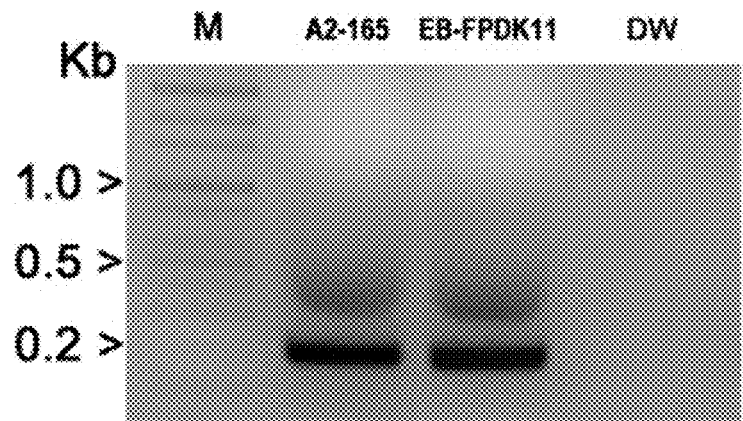
FIG. 2 shows the results of PCR analysis of the *Faecalibacterium prausnitzii* EB-FPDK11 strain of the present invention and the type strain *Faecalibacterium prausnitzii* A2-165 strain.

In order to confirm whether the isolated strain is a *Faecalibacterium prausnitzii* strain, the isolated strain was subjected to PCR analysis using the FP-specific primers (SEQ ID NO: 2 and SEQ ID NO: 3) shown Table 1 below. As a result, as shown in FIG. 2, it could be confirmed that the isolated strain showed a band pattern similar to that of the type strain *Faecalibacterium prausnitzii* A2-165 strain.

TABLE 1

| Desig-nation | Direc-tion | Sequence (5'→3') | Amplicon size | SEQ ID NO |
|---|---|---|---|---|
| FP1 | Forward | ACT CAA CAA GGA AGT GA | 192 bp | SEQ ID NO: 2 |
| FP2 | Reverse | CAG AGG TAG GCG GAA TT | 192 bp | SEQ ID NO: 3 |

1.4. Random Amplified Polymorphic DNA (RAPD) Analysis

In order to verify whether the *Faecalibacterium prausnitzii* EB-FPDK11 strain isolated as described above would be the same as the previously reported type strain *Faecalibacterium prausnitzii* A2-165 strain of the same species, RAPD, a kind of molecular typing, was performed. To this end, the genomic DNA extracted from the isolated strain was amplified using the universal primers shown in Table 2 below, and then electrophoresed on 1% agarose gel for 1 hour and 30 minutes, and the DNA fragment patterns were compared on a UV transilluminator. The results are shown in FIG. 3.

TABLE 2

| Desig-nation | Direc-tion | Sequence (5'→3') | SEQ ID NO |
|---|---|---|---|
| ERIC-1 | Forward | ATG TAA GCT CCT GGG GAT TCA C | SEQ ID NO: 4 |
| ERIC-2 | Reverse | AAG TAA GTG ACT GGG GTG AGC G | SEQ ID NO: 5 |
| (GTG)₅ | Forward/ Reverse | GTG GTG GTG GTG GTG | SEQ ID NO: 6 |

Figure 3:
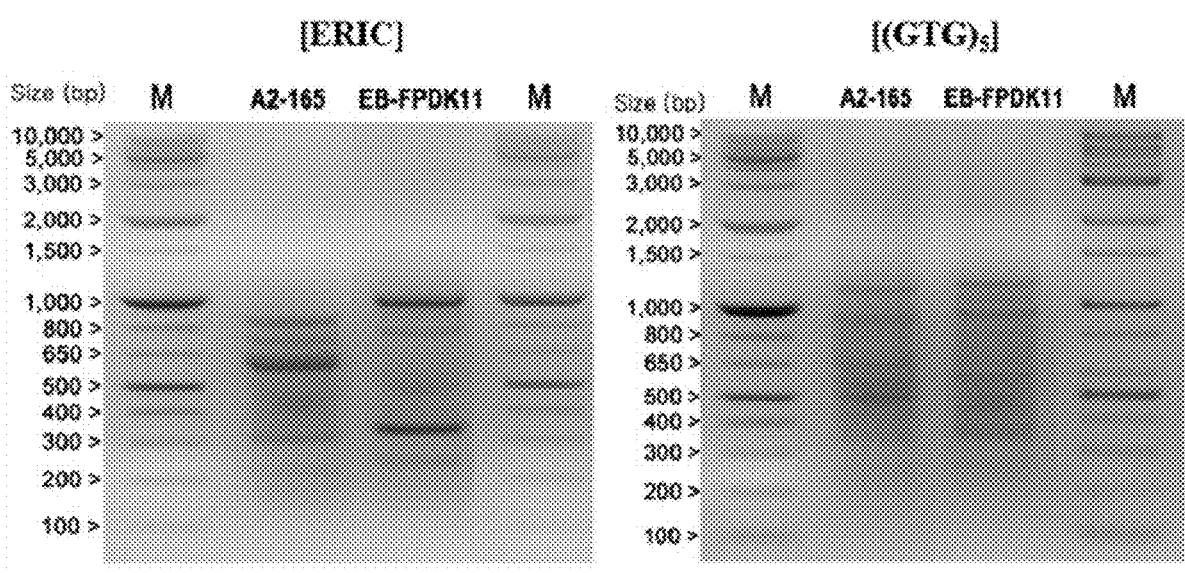
FIG. 3 shows the results of RAPD (Random Amplified Polymorphic DNA) analysis of the genomic DNAs of the *Faecalibacterium prausnitzii* EB-FPDK11 strain of the present invention and the type strain *Faecalibacterium prausnitzii* A2-165 strain.

As can be seen in FIG. 3, the *Faecalibacterium prausnitzii* EB-FPDK11 strain of the present invention showed a RAPD band pattern different from that of the type strain *Faecalibacterium prausnitzii* EB-FPDK11 A2-165. Thus, it was confirmed that the *Faecalibacterium prausnitzii* EB-FPDK11 strain of the present invention was a strain different from the type strain *Faecalibacterium prausnitzii* A2-165, even though it was of the same species as the type strain *Faecalibacterium prausnitzii* A2-165.

1.5. 16S rRNA BLAST

In order to confirm whether the isolated strain is a *Faecalibacterium prausnitzii* strain, the 16S rRNA nucleotide sequence thereof was analyzed and then evaluated by BLAST (Basic local alignment search tool). As a result, it was confirmed that the isolated strain was at least 99% identical to *Faecalibacterium prausnitzii* species.

1.6. Phylogenetic Tree Analysis of Full-Length 16S rRNA Gene Sequences

For full-length 16S rRNA gene sequencing of the *Faecalibacterium prausnitzii* EB-FPDK11 strain isolated as described above, the 16S rRNA gene was amplified using the 27F and 1492R primers shown in Table 3 below, and then sequencing thereof was performed using the 3730xl DNA analyzer. A phylogenetic tree was prepared using the EB-FPDK11 strain gene sequence obtained as described above and already published 16S rRNA gene sequences of other strains of the same species, and is shown in FIG. 4.

TABLE 3

| Designation | Direction (5′→3′) | Sequence (5′→3′) | Amplicon size | SEQ ID NO |
|---|---|---|---|---|
| 27F | Forward | AGA GTT TGA TCM TGG CTC AG | 1,465 bp | SEQ ID NO: 7 |
| 1492R | Reverse | GGT TAC CTT GTT ACG ACT T | 1,465 bp | SEQ ID NO: 8 |

Figure 4:
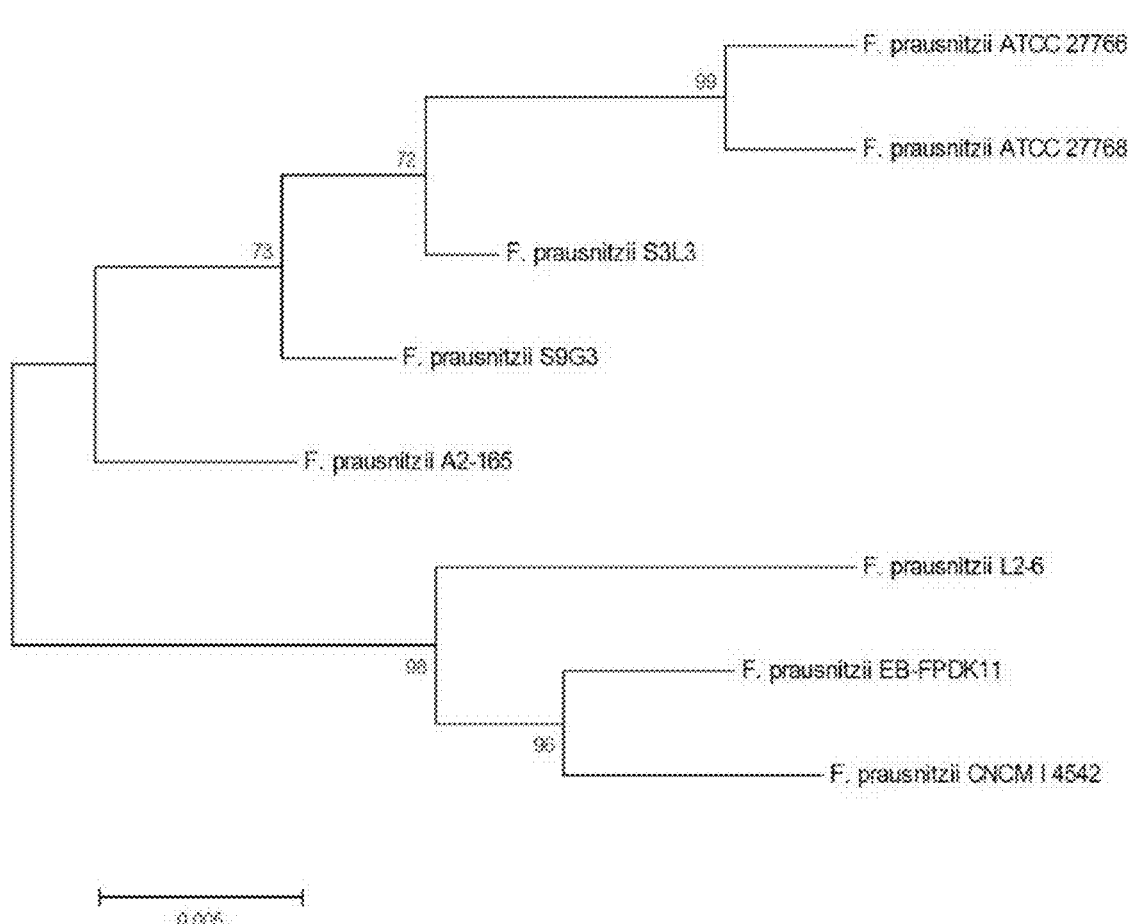
FIG. 4 shows the phylogenetic relationship between the *Faecalibacterium prausnitzii* EB-FPDK11 strain of the present invention and other *Faecalibacterium prausnitzii* strains.

As shown in FIG. 4, as a result of analyzing the evolutionary relationship between the strains through the phylogenetic tree analysis following the 16s rRNA gene sequencing, it was confirmed that the *Faecalibacterium prausnitzii* EB-FPDK11 strain was a strain belonging to the *Faecalibacterium prausnitzii* species in genetics terms. The *Faecalibacterium prausnitzii* EB-FPDK11 strain isolated from the human feces was identified by a biochemical method (API) and a molecular biological method (16s rRNA sequencing, 16s rRNA BLAST analysis, and RAPD) using *Faecalibacterium prausnitzii* (A2-165) as a control, and it was confirmed through an antibiotic resistance test described below that the *Faecalibacterium prausnitzii* EB-FPDK11 strain is a safe strain capable of having the function of probiotics. Based on these results, the isolated *Faecalibacterium prausnitzii* strain was named "*Faecalibacterium prausnitzii* EB-FPDK11" strain, and was deposited with the Korean Culture Center of Microorganisms (KCCM) under accession number KCCM12621P.

Example 2: Analysis of Characteristics and Safety of *Faecalibacterium prausnitzii* EB-FPDK11 Strain

2.1. Analysis of Functional Metabolites (Short Chain Fatty Acids)

The contents of short chain fatty acids (SCFA) contained in the culture medium were analyzed by gas chromatography to confirm the functional metabolites of the isolated *Faecalibacterium prausnitzii* EB-FPDK11 strain. To this end, the strain was cultured in YBHI medium [brain-heart infusion medium supplemented with 0.5% w/v yeast extract (Difco), 0.1% w/v Dcellobiose, 0.1% w/v D-maltose) for 24 hours, and then centrifuged at 12,000×g for 5 minutes, and the supernatant was collected. The supernatant was filtered through a 0.2-μm syringe filter and then used in analysis. Analysis was performed using gas chromatography (Agilent 7890N) equipped with a FFAP column (30 mX0.320 mm, 0.25 μm phase) under the conditions shown in Table 4 below.

TABLE 4

| | |
|---|---|
| Flow | $H_2$: 40 mℓ /min, Air: 350 mℓ /min |
| Injector temp. | 240° C. |
| Detector temp. | 250° C. |
| Oven temp. | 40° C. (hold 2 min) → |
| | 65° C./10 min (hold 2 min) → |
| | 240° C./10 min (hold 5 min) |
| Injection vol. | 2 μℓ |
| Split ratio | 20:1 |

Figures 5, 6:
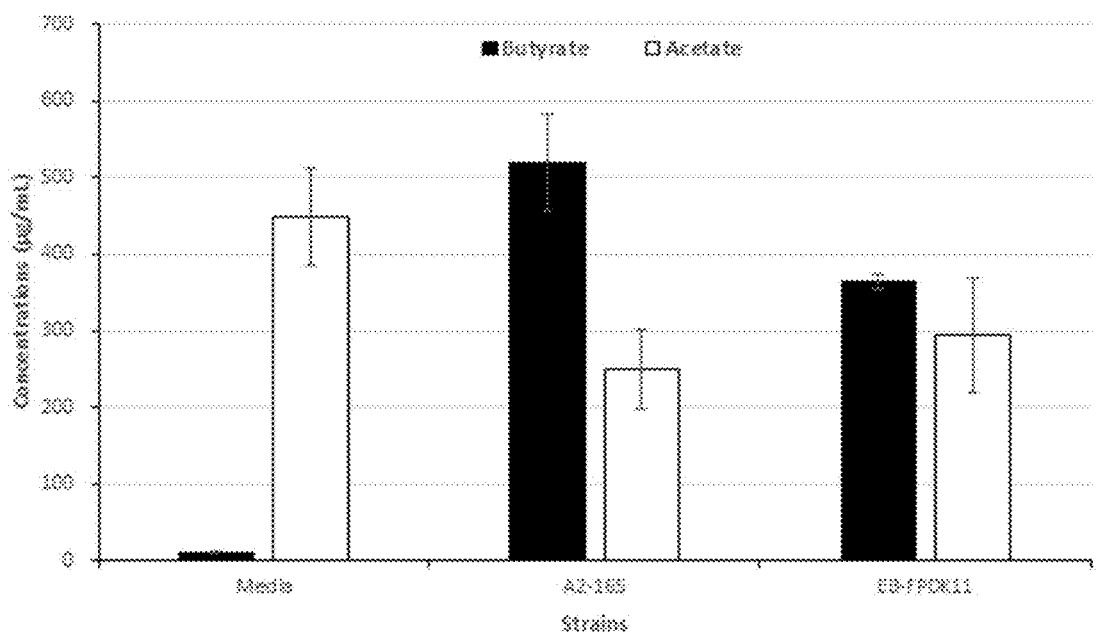
FIG. 5 is a graph showing the results of analyzing the short-chain fatty acids of the *Faecalibacterium prausnitzii* EB-FPDK11 strain of the present invention and other *Faecalibacterium prausnitzii* strains.
FIG. 6 shows the results of a hemolytic activity test for the *Faecalibacterium prausnitzii* EB-FPDK11 strain of the present invention and other *Faecalibacterium prausnitzii* strains.

As can be seen from FIG. 5, as a result of analysis of functional metabolites (short chain fatty acids), it was confirmed that the *Faecalibacterium prausnitzii* EB-FPDK11 strain of the present invention consumes acetate and produces butyrate.

2.2. Examination of Antibiotic Sensitivity

In order to examine the antibiotic sensitivity of the *Faecalibacterium prausnitzii* EB-FPDK11 strain isolated as described above, the minimum inhibitory concentrations (MICs) of piperacillin-tazobactam (PTZ), ceftidoxime (CTZ), chloramphenicol (CHL), clindamycin (CLI), meropenem (MEM), moxifloxacin (MXF), metronidazole (MTZ), and ciprofloxacin (CIP), which are antibiotics for anaerobic bacteria, were determined according to the broth microdilution method of the Clinical & Laboratory Standard Institute (CLSI) guideline (CLSI, 2017), and the results are shown in Table 5 below.

TABLE 5

| | MIC[a] Breakpoints (μg/ mℓ) | | | QC ATCC | Test strain | |
|---|---|---|---|---|---|---|
| Antibiotic | S | I | R | 29741[b] | A2-165 | EB-FPDK11 |
| PTZ | ≤32/4 | 64/4 | ≥128/4 | 8/4 | ≤256/4 (R) | ≤256/4 (R) |
| CTZ | ≤32 | 64 | ≥128 | 16 | 64 (I) | 128 (R) |
| CHL | ≤8 | 16 | ≥32 | 8 | 64 (R) | 8 (S) |
| CLI | ≤2 | 4 | ≥8 | 4 | ≤0.125 (S) | ≤0.125 (S) |
| MEM | ≤4 | 8 | ≥16 | 0.5 | >64 (R) | >64 (R) |
| MXF | ≤2 | 4 | ≥8 | 8 | 16 (R) | 32 (R) |
| MTZ | ≤8 | 16 | ≥32 | 2 | 4 (S) | 0.5 (S) |
| CIP | ≤1 | 2 | ≥4 | >32 | 32 (R) | 16 (R) |

PTZ: Piperacillin-tazobactam,
CTZ: ceftizoxime (3rd gen),
CHL: chloramphenicol,
CLI: clindamycin,
MEM: meropenem,
MXF: moxifloxacin (4th gen),
MTZ: metronidazole,
CIP: ciprofloxacin (2nd gen),
[a]MIC: minimal inhibitory concentration,
[b]*Bacteroides thetiotaomicron* ATCC 29741

As can be seen in Table 5 above, the *Faecalibacterium prausnitzii* EB-FPDK11 strain of the present invention exhibited resistance to piperacillin-tazobactam (PTZ), ceftizoxime (CTZ) and meropenem (MEM), and moxifloxacin (MXF) and ciprofloxacin (CIP), which are fluoroquinolone antibiotics, and showed sensitivity to chloramphenicol (CHL), clindamycin (CLI) and metronidazole (MTZ). The antibiotic resistance of the *Faecalibacterium prausnitzii* EB-FPDK11 strain to chloramphenicol (CHL) antibiotic did significantly differ from that of the type strain (A2-165).

2.3. Analysis of Hemolytic Activity

To verify the safety of the *Faecalibacterium prausnitzii* EB-FPDK11 strain isolated as described above, whether the strain has hemolytic activity and cytotoxicity was evaluated. To this end, the strain was cultured using a blood agar medium prepared by adding 5% w/v defibrinated sheep blood to tryptic soy agar (17.0 g/L pancreatic digest of casein, 3.0 g/L pancreatic digest of soybean, 2.5 g/L dextrose, 5.0 g/L sodium chloride, 2.5 g/L potassium phosphate, 15 g/L agar), and the results are shown in FIG. 6.

As can be seen in FIG. 6, it was confirmed that the *Faecalibacterium prausnitzii* EB-FPDK11 strain of the present invention did not show a completely transparent part around the colony, suggesting that the strain does not cause β-hemolysis associated with pathogenicity.

Example 3: Confirmation of Effect of *Faecalibacterium prausnitzii* Strain on Treatment of Atopic Disease

3.1. Strain Sample

The *Faecalibacterium prausnitzii* A2-165 strain and *Faecalibacterium prausnitzii* EB-FPDK11 live bacteria used in this experiment were prepared at a concentration of $1 \times 10^8$ CFU/150 μl PBS (25% glycerol, 0.05% cysteine/PBS).

3.2. Animal Model and Sampling

To observe atopic dermatitis lesions, 6-week-old NC/Nga mice (weighed about 21 to 25 g, SLC, Inc., Japan) were purchased from Daehan Biolink Co., Ltd. (Chungbuk, Korea). Animal tests were carried out in accordance with the Animal use and Care Protocol of the Institutional Animal Care and Use Committee (IACUC). The animals were acclimated for one week, and then raised for 9 weeks at a constant temperature of 22° C. and a relative humidity of 50 to 60% with a 12-hr light/12-hr dark cycle.

3.3. Induction of Atopic Dermatitis

The backs of 6-week-old NC/Nga mice were shaved clean, and then left to stand for 24 hours so that fine wounds of the skin were healed. 1% 2,4-dinitrochlorobenzene (DNCB) solution (Sigma-Aldrich Korea) was applied to the back of each mouse twice a week for 3 weeks to induce an immune response, and then 0.5% DNCB solution was applied twice a week to induce contact dermatitis. DNCB used in this Example was diluted at 0.5% and 1% in a solution obtained by mixing acetone and olive oil at 3:1.

Each of the corresponding drugs was administered orally daily for 6 weeks after induction of atopic dermatitis. As a positive control, dexamethasone was diluted with distilled water to a concentration of 60 μg/ml and administered orally in an amount of 200 μl daily (see Table 6).

TABLE 6

| Group | Administration group | Drug administered |
|---|---|---|
| Group I | Normal group | PBS |
| Group II | Atopic dermatitis control group (DNCB-induced atopic dermatitis) | PBS |
| Group III | A2-165 type strain-administered group | A2-165 live bacteria, $1 \times 10^8$ CFU |
| Group IV | EB-FPDK11 strain-administered group | EB-FPDK11 live bacteria, $1 \times 10^8$ CFU |
| Group V | Positive control group (dexamethasone-administered group) | 60 μg/μl, 200 μl |

3.4. Evaluation of Atopic Dermatitis

Figure 7:
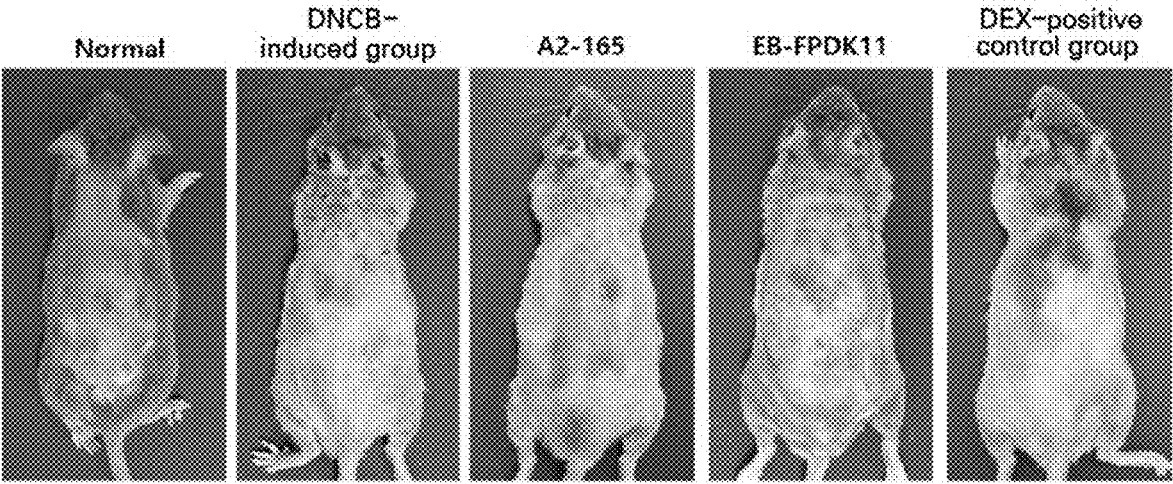
FIG. 7 depicts photographs showing the skin conditions of experimental animals with induced atopic dermatitis when treated with the *Faecalibacterium prausnitzii* EB-FPDK11 strain of the present invention.
Figure 8:
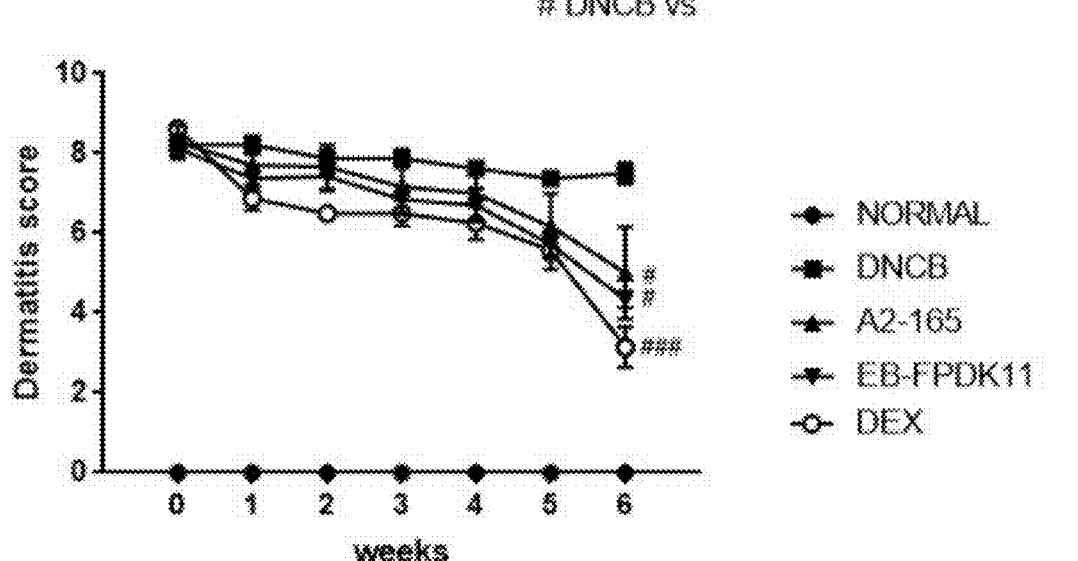
FIG. 8 is a graph showing the change in dermatitis score caused by the *Faecalibacterium prausnitzii* EB-FPDK11 strain of the present invention.

After atopic dermatitis was induced by DNCB, treatment was performed by administering a preparation containing each of dexamethasone (DEX), the A2-165 strain and the EB-FPDK11 strain for 6 weeks. To examine the clinical symptoms, the skin condition and the dermatitis score obtained by scoring the same were checked. Sensory evaluation was performed using a modification of the SCORAD (Scoring Atopic Dermatitis) index which is a clinical visual evaluation method which is commonly used for atopic dermatitis. Skin dryness, edema, erythema/hemorrhage, and erosion/excoriation were scored as follows: no symptoms=0, weak symptoms=1, moderate symptoms=2, and severe symptoms=3. Evaluation was performed every week, and the evaluation results are shown in FIGS. 7 and 8.

As a result of measuring the dermatitis score by visually observing the skin condition of each group during the 6-week treatment period, it could be confirmed that, in the atopic dermatitis-induced group (DNCB), the symptoms of atopic dermatitis were maintained for 6 weeks, whereas, in the experimental groups to which each of the A2-165 strain, the EB-FPDK11 strain and dexamethasone (DEX) was administered, the symptoms of atopic dermatitis significantly decreased.

As a result of numerical evaluation based on the dermatitis score at week 6, it could be confirmed that decreases in dermatitis score of 32.5% and 30.9% for 6 weeks compared to the atopic dermatitis-induced group appeared in the group to which the type strain A2-165 was administered (P=0.02) and the group to which the EB-FPDK11 of the present invention was administered (P<0.02), respectively. It was confirmed that the group to which the EB-FPDK11 strain of the present invention was administered exhibited a better effect of ameliorating atopic skin conditions than the group to which the type strain *Faecalibacterium prausnitzii* was administered.

3.5. Effect of Strain on Ear Edema Caused by Atopic Dermatitis

Figure 9:
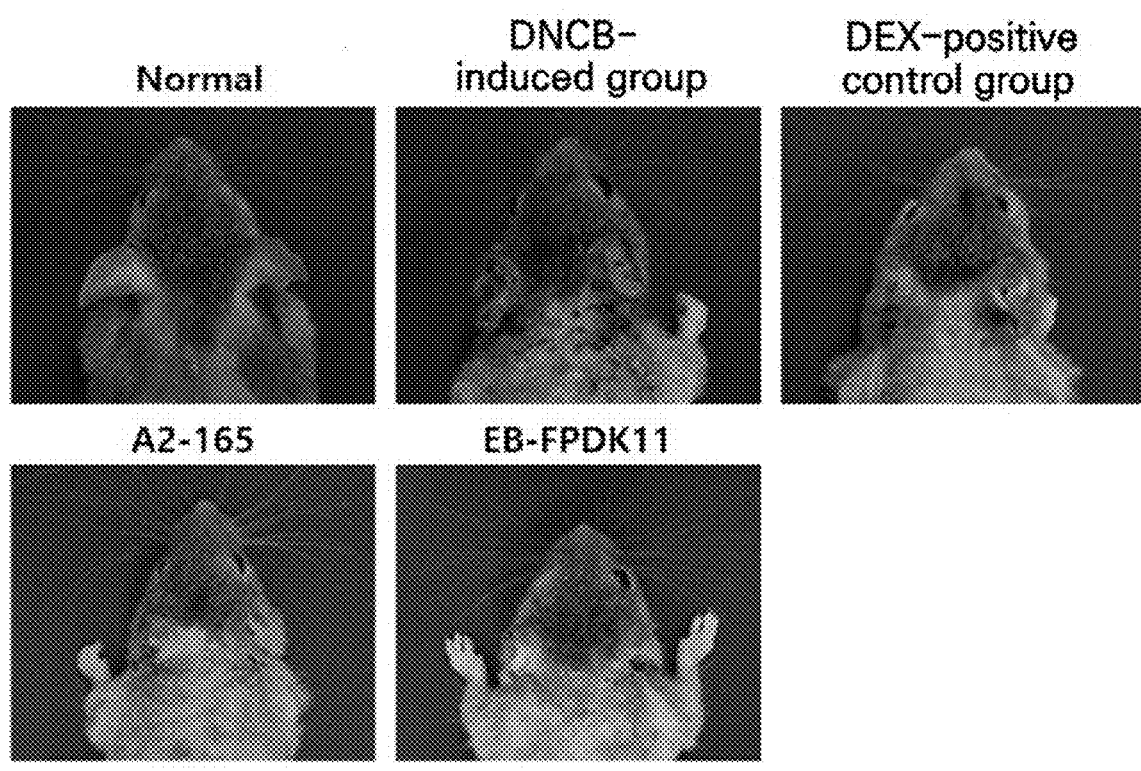
FIG. 9 depicts photographs showing a comparison of the degree of ear edema between the group (EB-FPDK11) to which the *Faecalibacterium prausnitzii* EB-FPDK11 strain of the present invention was administered, the positive control group (DEX) to which dexamethasone was administered, and the group to which the type strain *Faecalibacterium prausnitzii* A2-165 strain was administered.
Figure 10:
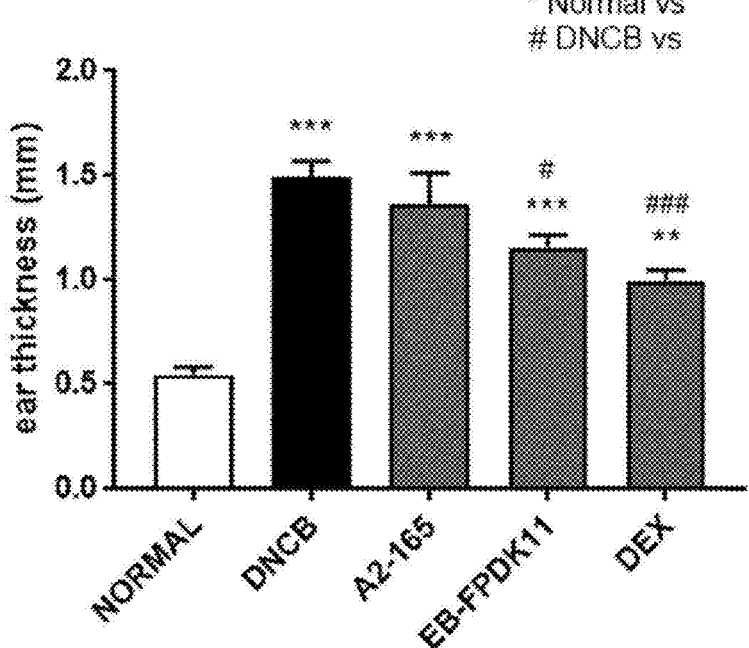
FIG. 10 shows the results of analyzing changes in ear thicknesses in the group to which the *Faecalibacterium prausnitzii* EB-FPDK11 strain of the present invention was administered, the positive control group (DEX), and the group to which the type strain *Faecalibacterium prausnitzii* A2-165 strain was administered.

After completion of the experiment, the mice were sacrificed by anesthetizing with $CO_2$, and then the degree of edema of both ears was measured by the velocity transformation technique using a thickness gauge (Digimatic thickness gauge, 547-301, Mitutoyo, Japan). The results of the measurement are shown in FIGS. 9 and 10.

Ear edema in the NC/Nga mice at 6 weeks was 0.55 mm in the normal group, 1.50 mm in the atopic dermatitis-induced group (DNCB), 1.37 mm in the A2-165-administered group, 1.16 mm (P=0.02) in the EB-FPDK11-administered group, and 1.00 mm (P<0.001) in the positive control group (DEX). As a result of observing the degree of atopic dermatitis in the state of ear edema, it was confirmed that the positive control group (DEX) showed the best effect of ameliorating atopic dermatitis, and the groups to which each of the type strain *Faecalibacterium prausnitzii* A2-165 and the EB-FPDK11 strain was administered all showed an excellent effect of ameliorating atopic dermatitis. Accordingly, it could be confirmed that the pharmaceutical composition of the present invention had a remarkable effect of inhibiting edema in the atopic dermatitis-induced mouse model.

3.6. Measurement of Scratching Score

Figure 11:
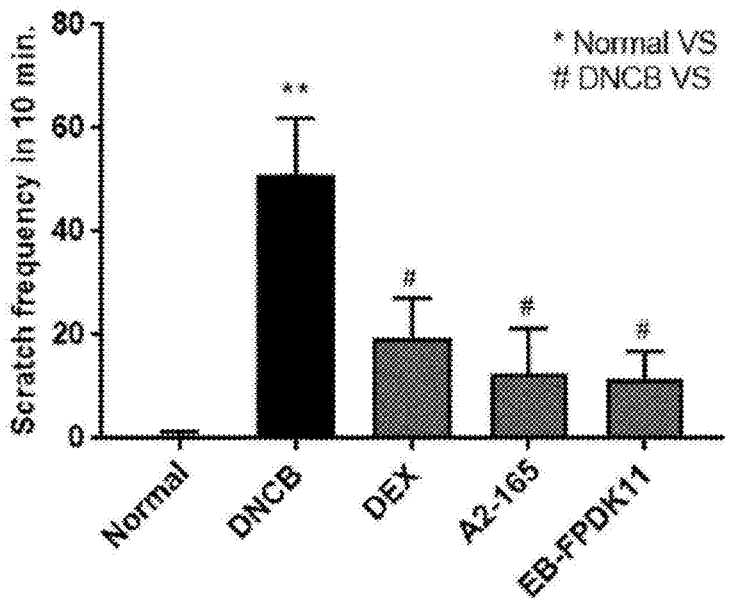
FIG. 11 is a graph showing the scratch frequency of experimental animals in the group to which the *Faecalibacterium prausnitzii* EB-FPDK11 strain of the present invention was administered, the positive control group (DEX), and the group to which the type strain *Faecalibacterium prausnitzii* A2-165 strain was administered.

The day before the end of the experiment, the frequency of scratching the affected area due to itching was measured. For measurement of the frequency of scratching, each mouse was acclimated for 10 minutes, and then the frequency of scratching for 10 minutes was measured using a counter. Scratching score in each mouse group is shown in FIG. 11.

The group with atopic dermatitis induced by treatment with DNCB showed a significantly increased frequency of scratching (P<0.001) compared to the normal group. It was confirmed that the frequencies of scratching in the group to which the type strain *Faecalibacterium prausnitzii* A2-165 was administered and the group to which the *Faecalibacterium prausnitzii* EB-FPDK11 of the present invention was administered decreased by 69.4% (P=0.01) and 76.19% (P=0.01), respectively, compared to that in the atopic dermatitis-induced group. The positive control group showed a decrease in scratching frequency of about 59.4% (P=0.03) compared to the atopic dermatitis-induced group (DNCB). Therefore, it was confirmed that the group to which the *Faecalibacterium prausnitzii* EB-FPDK11 of the present invention was administered showed a better antipruritic effect than the positive control group to which dexamethasone was administered or the group to which the type strain *Faecalibacterium prausnitzii* A2-165 was administered.

3.7. Measurement of Spleen Weight and Size

The spleen exhibits the characteristics of both primary and secondary lymphoid organs, is composed of a red pulp that filters red blood cells and a white pulp that exhibits humoral and cellular immunity, and is another important organ for immune responses (Mebius, R E and Kraal, G 2005 Structure and function of the spleen Nat Rev Immunol 5, pp. 606-616). In addition, the spleen is where the final stage of B cell development occurs, and at the same time, the spleen functions as a specialized organ that responds to antigens derived from blood (Boehem, T and Bleul, CC 2007 The evolutionary history of lymphoid organs Nat Immunol 8, 131-135). The response of atopic dermatitis may induce various responses in the immune system, and these responses may primarily affect the weight of the spleen that is an immune organ.

Figure 12:
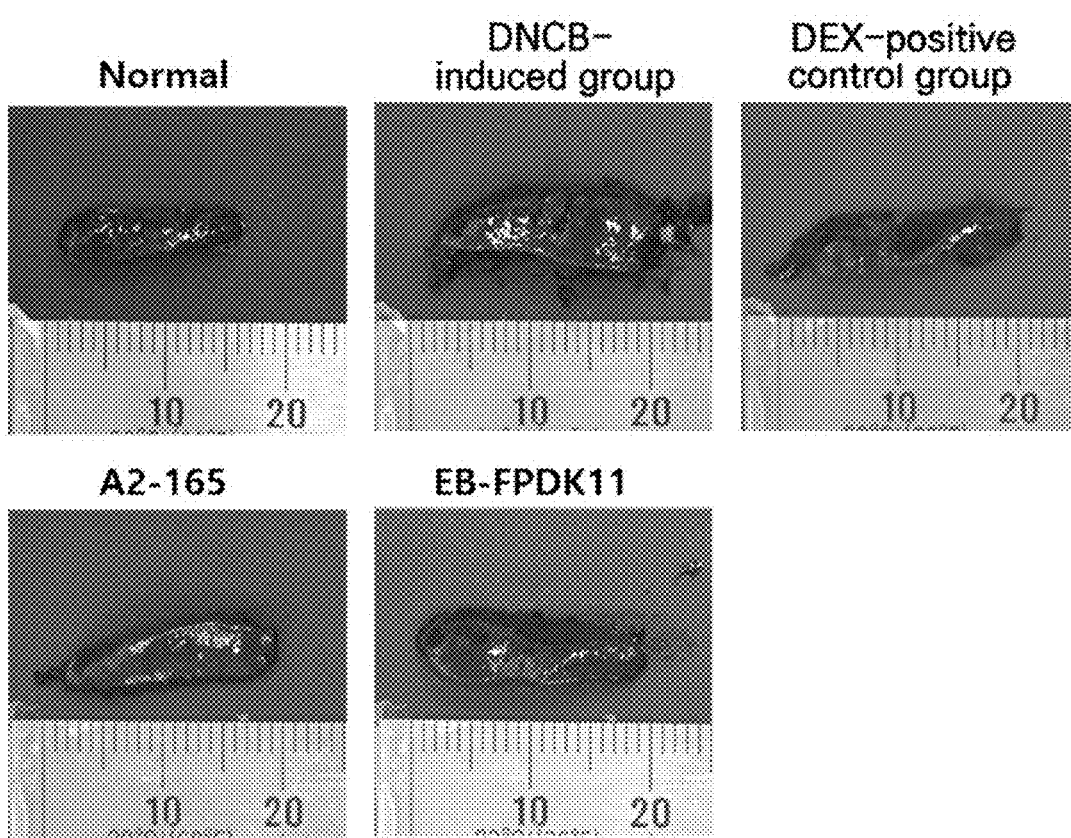
FIG. 12 depicts photographs of the spleens of the group to which the *Faecalibacterium prausnitzii* EB-FPDK11 strain of the present invention was administered, the positive control group (DEX), and the group to which the type strain *Faecalibacterium prausnitzii* A2-165 strain was administered.
Figure 13:
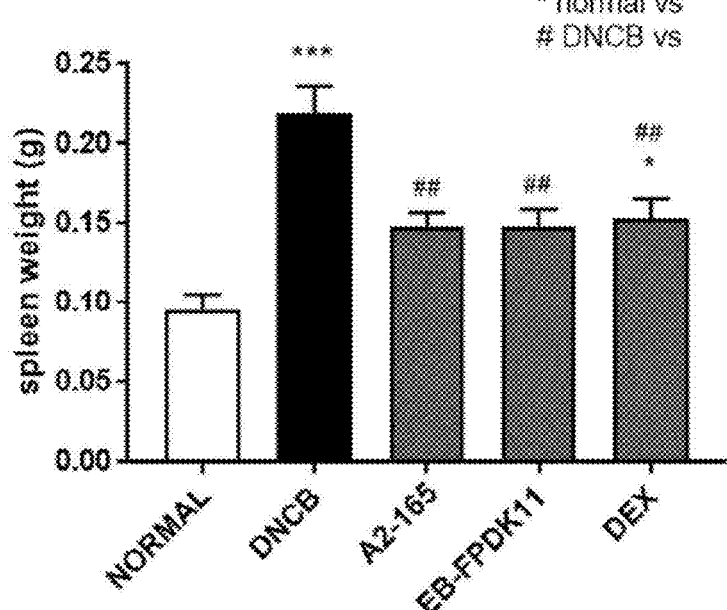
FIG. 13 is a graph showing a comparison of spleen weight between the group to which the *Faecalibacterium prausnitzii* EB-FPDK11 strain of the present invention was administered, the positive control group (DEX), and the group to which the type strain *Faecalibacterium prausnitzii* A2-165 strain was administered.

Thus, the weight of the spleen was measured to observe the effect of the composition for preventing atopic dermatitis on the immune organs of NC/Nga mice with atopic dermatitis induced by DNCB. More specifically, after completion of the experiment, the experimental animals were anesthetized with $CO_2$ and sacrificed by cervical dislocation, and the abdomens thereof were opened, and spleen tissue was collected. The collected spleen tissue was washed with physiological saline and then dried, and the weights thereof were measured using a microbalance and the sizes thereof were visually observed. The results are shown in FIGS. 12 and 13.

The spleen weight of the atopic dermatitis-induced group (DNCB) increased about 2 times compared to the normal group (P<0.001), and the type strain A2-165-administered group, the EB-FPDK11 strain-administered group and the dexamethasone-administered group showed decreases in spleen weight of 17.37% (P=0.010), 19.98% (P=0.0006) and 23.26% (P=0.007), respectively, compared to the atopic dermatitis-induced group (DNCB). In particular, both the groups to which the type strain *Faecalibacterium prausnitzii* A2-165 and the EB-FPDK11 strain of the present invention showed an effect similar to the positive control group (DEX). Therefore, it can be confirmed that the composition containing the EB-FPDK11 of the present invention has an excellent immunosuppressive effect.

3.8. Measurement of Serum IgE Concentration

Figure 14:
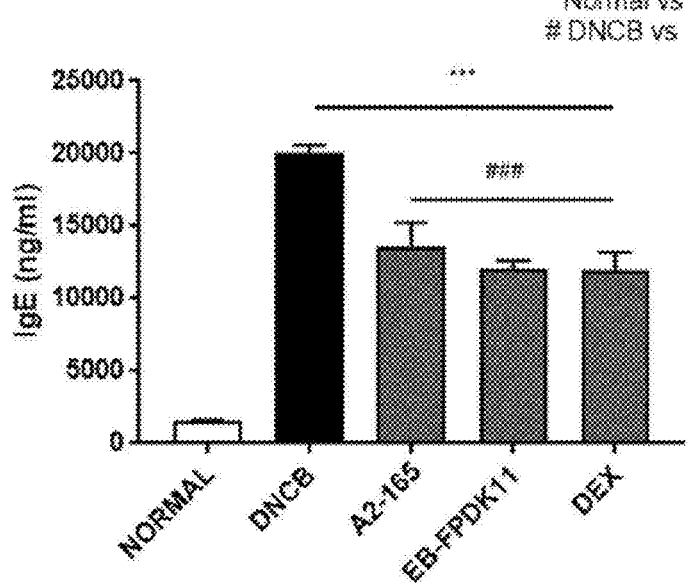
FIG. 14 is a graph showing changes in IgE, which is the most important immune marker that mediates allergic disease, the group to which the *Faecalibacterium prausnitzii* EB-FPDK11 strain of the present invention was administered, the positive control group (DEX), and the group to which the type strain *Faecalibacterium prausnitzii* A2-165 strain was administered.

At the end of the experiment, each of the mice was anesthetized with $CO_2$ and blood was collected by cardiac puncture. The collected blood was centrifuged at 10,000 rpm for 5 minutes to separate the serum, and the serum IgE concentration was measured. The results of the measurement are shown in FIG. 14. The IgE concentration measurement was performed using an ELISA kit (IgE mouse uncoated ELISA kit cat #88-50460, Invitrogen, CA, USA).

Referring to FIG. 14, the serum IgE concentration in the atopic dermatitis-induced group (DNCB) increased about 13 times (1545.08 ng/ml, P<0.001) compared to that in the normal group, but the serum IgE concentrations in both the group to which the type strain *Faecalibacterium prausnitzii* A2-165 was administered and the group to which the *Faecalibacterium prausnitzii* EB-FPDK11 strain of the present invention was administered significantly decreased compared to that in the atopic dermatitis-induced group (DNCB). It was confirmed that the serum IgE concentrations in the A2-165 strain-administered group, the EB-FPDK11 strain-administered group and the dexamethasone-administered groups significantly decreased 32.23%, 40.00% and 40.70%, respectively, compared to that in the atopic dermatitis-induced group (DNCB) (P<0.001). Therefore, it was confirmed that the composition containing the EB-FPDK11 strain of the present invention has an IgE production inhibitory effect comparable to that of dexamethasone, and is highly effective in alleviating atopic symptoms.

3.9. Histopathological Observation

At the end of the experiment, each of the mice was sacrificed, and the skin was isolated, fixed in 10% formaldehyde solution, and embedded in paraffin, and the paraffin block was sectioned. The paraffin sections were stained with hematoxylin & eosin (H&E), and changes in the thicknesses of the epidermal layer and the dermal layer were observed with an optical microscope at 200× magnification. The results are shown in FIG. 15.

Figure 15:
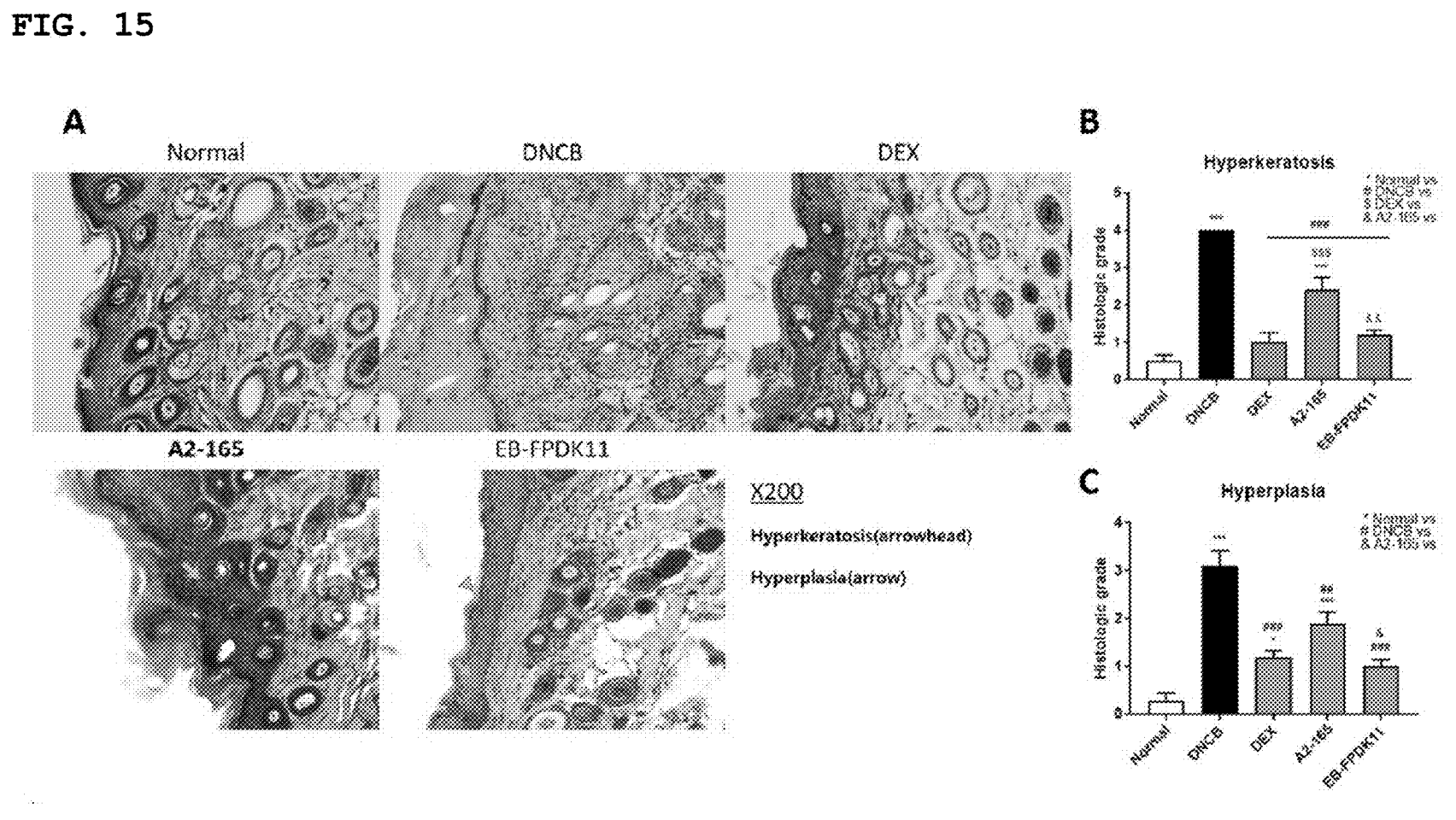

As a result of observing the back skin tissue of the NC/Nga mice by H&E staining, as shown in FIG. 15, the atopic dermatitis-induced group (DNCB) showed thickening of the epidermal layer toward the dermal layer, and histopathological findings, including severe damage to the skin barrier and increased infiltration of inflammatory cells, compared to the atopic dermatitis-induced group (DNCB). In addition, microscopic observation indicated that all the *Faecalibacterium prausnitzii*-administered groups and the positive control group (DEX group) showed histopathological features similar to those of the normal group, because they showed decreased infiltration of inflammatory cells, and thickening of both the epidermal layer and the dermal layer therein, which is observed upon induction of atopic dermatitis, was inhibited.

Hyperkeratosis and hyperplasia shown in FIG. 15(A) were histologically graded as follows: the thickness of the normal group=0; 2 times the thickness of the normal group=1; 3 times=2; 4 times=3; and 4 times or more=4.

As shown in the graphs of FIGS. 15(B) and 15(C), it was confirmed that hyperkeratosis and epithelial hyperplasia significantly increased 3 to 4 times in the atopic dermatitis-induced group (DNCB) compared to the normal group, and were significantly inhibited in the positive control group, the group to which the type strain *Faecalibacterium prausnitzii* A2-165 was administered and the group to which the *Faecalibacterium prausnitzii* EB-FPDK11 of the present invention was administered, compared to the atopic dermatitis-induced group (DNCB).

3.10. Measurement of Serum Cytokine Concentrations

After induction of atopic dermatitis, the concentrations of cytokines related to Th1 and Th2 were measured to examine the immune response resulting from administration of the *Faecalibacterium prausnitzii* EB-FPDK11 strain of the present invention. For statistics for all experiments, one-way ANOVA was performed using GraphPad Prism 7.04.

Figure 16:
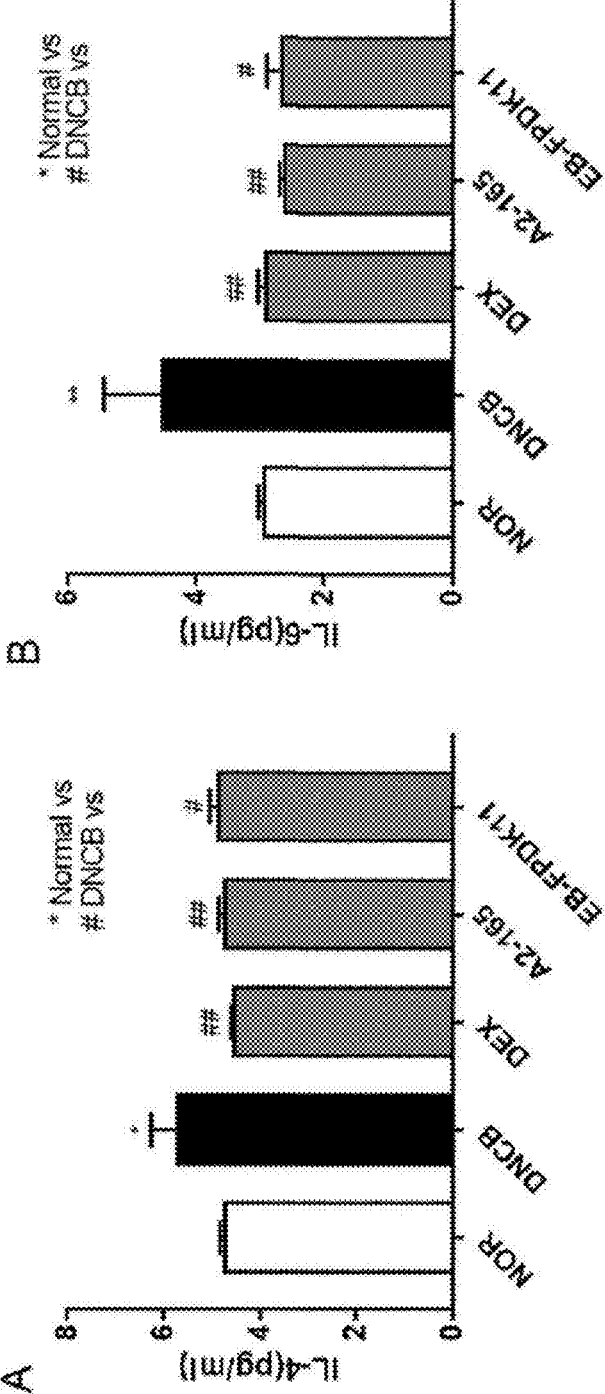
FIGS. 16A and 16B show the results of evaluating the effects of administration of the *Faecalibacterium prausnitzii* EB-FPDK11 strain of the present invention on IL-4 and IL-6.
Figure 17:
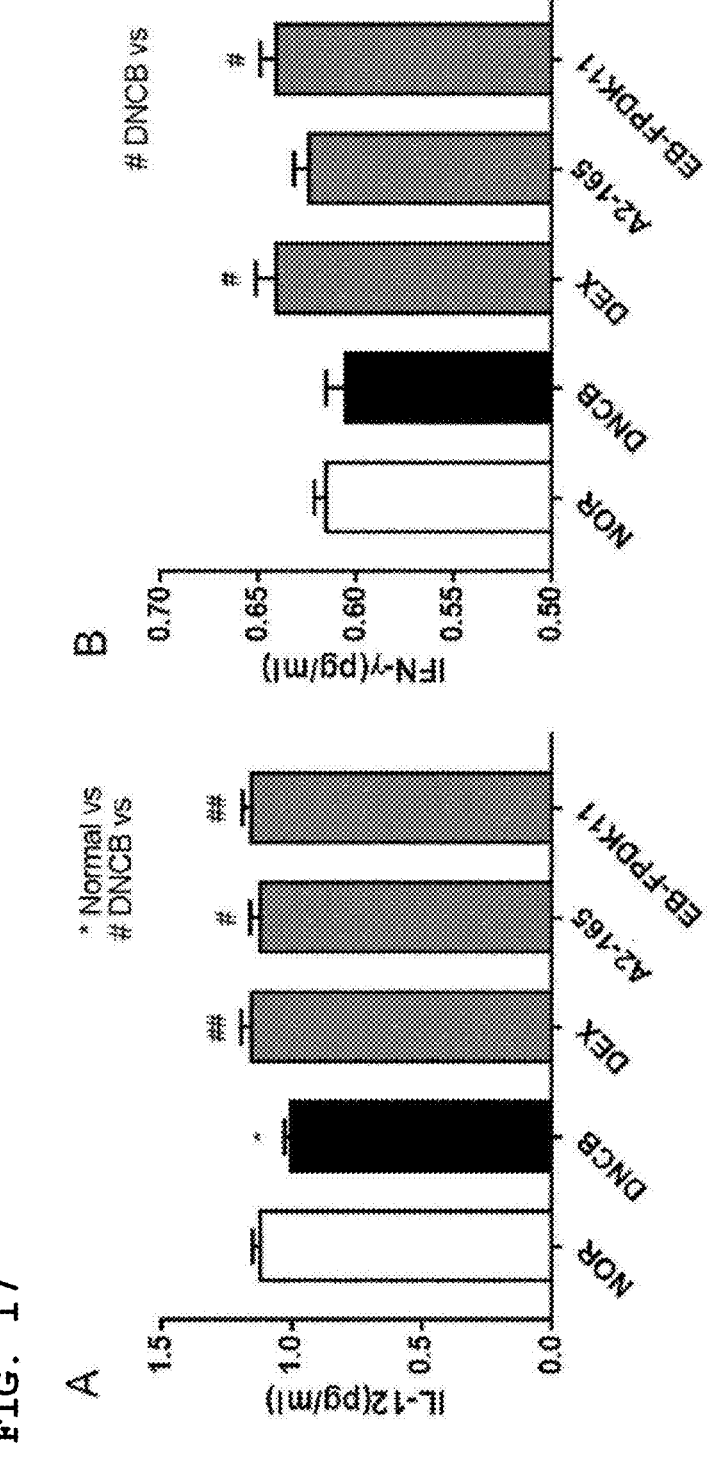
FIGS. 17A and 17B show the results of evaluating the effects of administration of the *Faecalibacterium prausnitzii* EB-FPDK11 strain of the present invention on blood Th1 cytokines IFN-γ and IL-12.

At the end of the experiment, the mice were anesthetized with $CO_2$, and blood was collected by cardiac puncture. The collected blood was centrifuged at 10,000 rpm for 10 minutes, and the serum was separated and stored at −80° C. The concentrations of IL-4, IL-12, IFN-γ and IL-6 cytokines were measured using an ELISA kit (Invitrogen, CA, USA), and the results of the measurement are shown in FIGS. 16 and 17.

First, the concentrations of the cytokines IL-4 and IL-6, which are induced by Th2 cell activity and also known as indicators of inflammatory response, were examined. As shown in FIG. 16(A), the IL-4 concentration increased 20.54% (P=0.02) in the atopic dermatitis-induced group (DNCB) compared to the normal group. In addition, the IL-4 concentration significantly decreased in all the positive control group (DEX), the group to which the type strain *Faecalibacterium prausnitzii* A2-165 was administered and the group to which the *Faecalibacterium prausnitzii* EB-FPDK11 of the present invention was administered, compared to that in the atopic dermatitis-induced group, and the IL-4 concentrations in these groups were similar to that in the normal group. In addition, as a result of measuring the mouse blood IL-6 concentration, it could be confirmed that the IL-6 concentration increased 1.54 times (P=0.009) in the atopic dermatitis-induced group (DNCB) compared to the normal group, and decreased 35.5% (P=0.009) in the positive control group (DEX), 41.8% (P=0.003) in the group to which the type strain *Faecalibacterium prausnitzii* A2-165 was administered, and 40.7% (P=0.01) in the group to which the *Faecalibacterium prausnitzii* EB-FPDK11 of the present invention, compared to the atopic dermatitis-induced group (DNCB) (see FIG. 16(B)).

3.11. Effect of EB-FPDK11 Strain on Blood Th1 Cytokines, IFN-γ and IL-12

In this experiment, the Th1 cytokine IFN-γ and its inducer IL-12 were measured. As a result, as shown in FIG. 17, it was confirmed that these cytokines all significantly increased in the *Faecalibacterium prausnitzii* EB-FPDK11-administered group. As a result of measuring the concentration of IL-12, it was confirmed that the concentration of IL-12 significantly decreased in the atopic dermatitis-induced group (DNCB) compared to the normal group (P=0.03), and significantly increased in the positive control group (P=0.008), the type strain *Faecalibacterium prausnitzii* A2-165-administered group (P=0.03) and the EB-FPDK11-administered group (P=0.004) compared to the atopic dermatitis-induced group. In particular, it was confirmed that the concentration of IL-12 in the group to which the EB-FPDK11 of the present invention was administered more significantly increased even compared to that in the type strain A2-165-administered group. The concentration of IFN-γ in the mouse blood significantly increased in the positive control group (DEX) (P=0.03) and the *Faecalibacterium prausnitzii* EB-FPDK11-administered group (P=0.03) compared to the atopic dermatitis-induced group (DNCB). Therefore, it was confirmed that administration of the *Faecalibacterium prausnitzii* EB-FPDK11 of the present invention showed a better effect of inducing Th1 differentiation by promoting the production of serum IL-12 and IFN-γ than dexamethasone.

Figure 18:
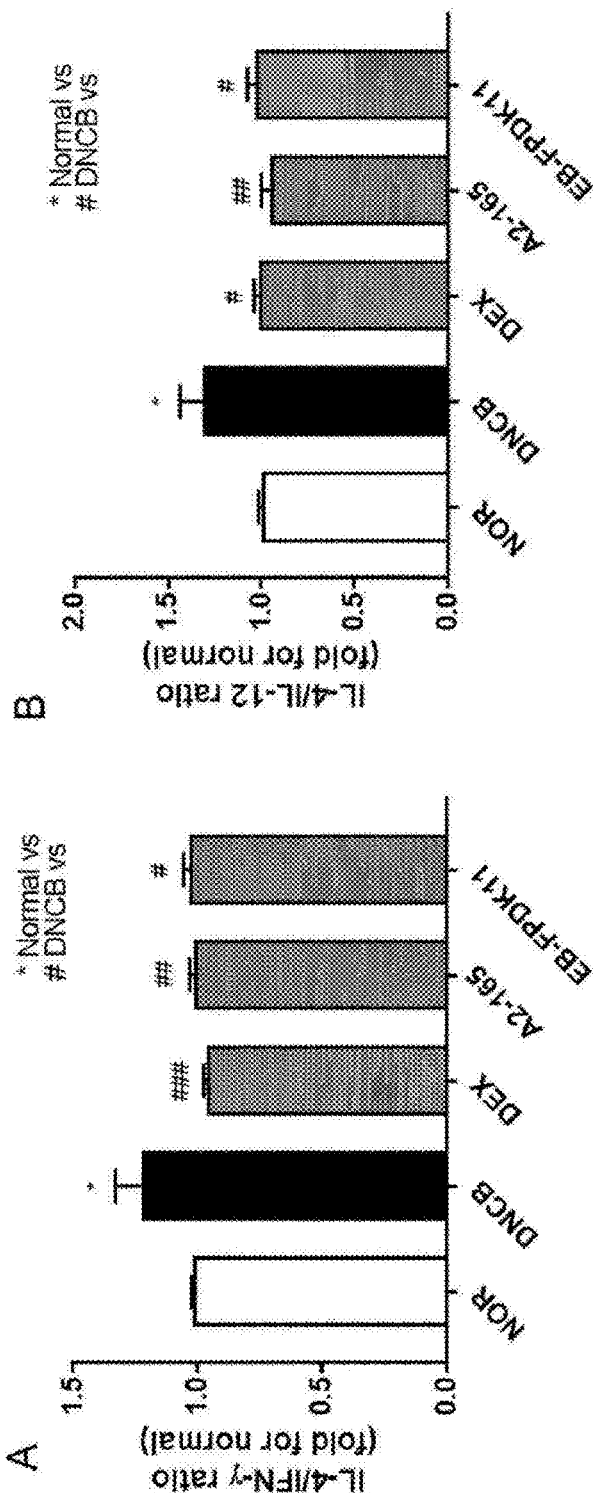
FIGS. 18A, 18B, 19A, and 19B show the results of evaluating the effects of administration of the *Faecalibacterium prausnitzii* EB-FPDK11 strain of the present invention on the production of blood Th1 cytokines and Th2 cytokines.

3.12. Effect of Administration of EB-FPDK11 Strain on Production of Th1 and Th2 Cytokines in Atopic Dermatitis Animal Model From an immunological point of view, allergenic atopic dermatitis is a disease caused by an excessive imbalance between Th1 and Th2 immune responses. Thus, the cytokine concentrations measured as described above were expressed as the ratio of Th2/Th1 cytokines, and the results are shown in FIGS. 18 and 19.

Referring to FIG. 18(A), as a result of analyzing the IL-4/IFN-γ ratio, it was confirmed that the IL-4/IFN-γ ratio in the atopic dermatitis-induced group (DNCB) significantly increased compared to that in the normal group, and the IL-4/IFN-γ ratio significantly decreased in both the type strain *Faecalibacterium prausnitzii* A2-165-administered group and the EB-FPDK11-administered group compared to the atopic dermatitis-induced group (DNCB), and the IL-4/IL-12 ratios in these groups were similar to that in the normal group. As a result of analyzing the IL-4/IL-12 ratio, it was confirmed that the IL-4/IL-12 ratio increased 35.4% (P=0.02) in the atopic dermatitis-induced group (DNCB) compared to the normal group. This indicates an increase in Th2 cytokine that typically appears in atopic dermatitis. In addition, it was confirmed that the IL-4/IL-12 ratio significantly decreased in all the positive control group, the type strain *Faecalibacterium prausnitzii* A2-165-administered group and the *Faecalibacterium prausnitzii* EB-FPDK11-administered group (DEX: 23.7% (P=0.02), A2-165: 30.4% (P=0.002), and EB-FPDK11: 23.0% (P=0.04)) (see FIG. 18(B)).

Figure 19:
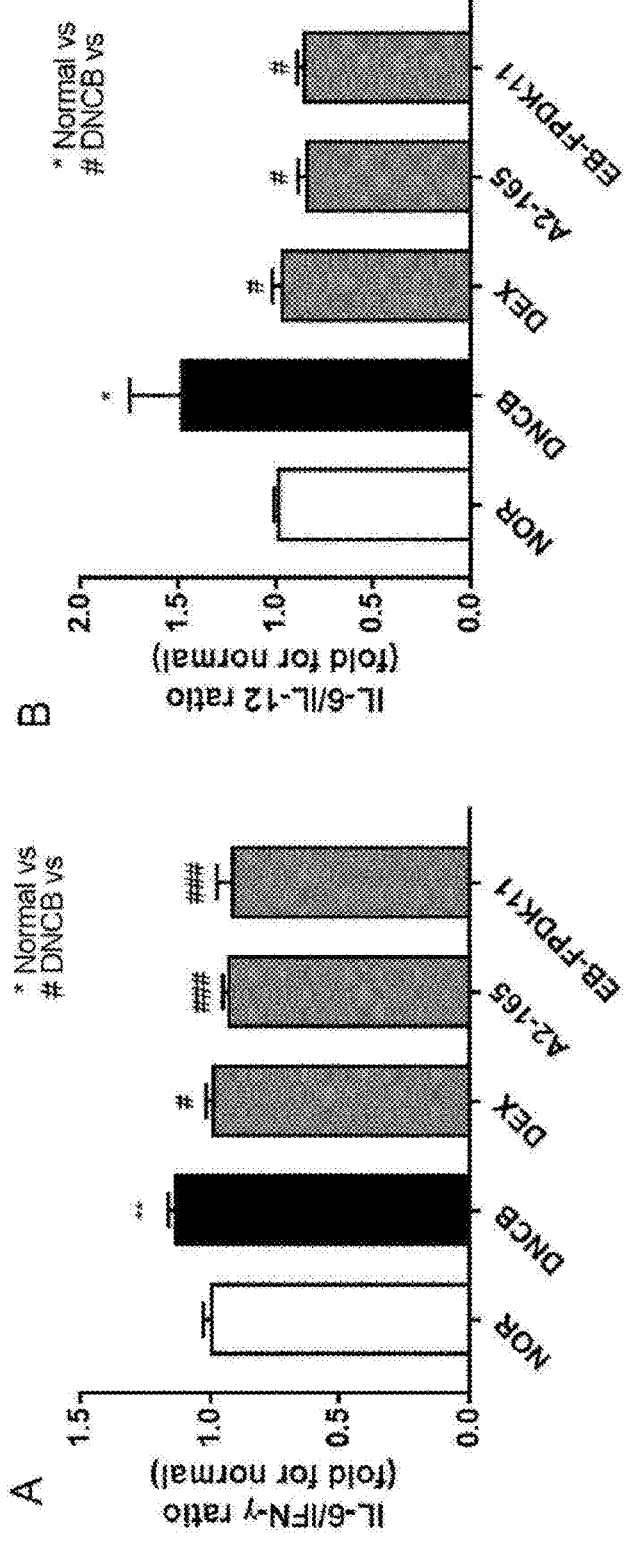

In addition, referring to FIG. 19, it could be confirmed that the results for the ratio of IL-6/IFN-γ and the ratio of IL-6/IL-12 were similar to the above-described results. It was confirmed that the ratio of IL-6/IFN-γ significantly increased in the atopic dermatitis-induced group (DNCB) compared to the normal group, and significantly decreased in all the positive control group (DEX), the type strain *Faecalibacterium prausnitzii* A2-165-administered group and the EB-FPDK11-administered group compared to the atopic dermatitis-induced group (DNCB) (see FIG. 19(A)).

Referring to FIG. 19(B), it was confirmed that the ratio of IL-6/IL-12 increased 58% (P=0.02) in the atopic dermatitis-induced group (DNCB) compared to the normal group, but decreased 35.8% (P=0.002) in the positive control group (DEX), 46.8% (P=0.01) in the type strain *Faecalibacterium prausnitzii* A2-165-administered group, and 44% (P=0.04) in the EB-FPDK11-administered group, compared to the atopic dermatitis-induced group (DNCB).

Taken together, it was confirmed that the ratios of IL-4/IFN-γ, IL-4/IL-12, IL-6/IFN-γ and IL-6/IL-12 increased in the atopic dermatitis-induced group and were inhibited by the *Faecalibacterium prausnitzii* EB-FPDK11 strain of the present invention. In other words, it was confirmed that administration of the *Faecalibacterium prausnitzii* EB-FPDK11 strain of the present invention inhibits the production of the Th2 cytokines IL-4 and IL-6, which is induced upon induction of atopic dermatitis, and as a result, controls excessive production of IgE. In addition, it is believed that the *Faecalibacterium prausnitzii* EB-FPDK11 strain of the present invention acts to effectively ameliorate atopic dermatitis by promoting the production of Th1 cytokines IFN-γ and IL-12 to balance Th1 and Th2 immune responses.

As described above, the pharmaceutical composition for preventing or treating atopic disease containing, as an active ingredient, the *Faecalibacterium prausnitzii* EB-FPDK11 strain according to the present invention, has an excellent effect of treating atopic disease, and particularly, significantly overcomes the limitations of conventional probiotic preparations, and exhibits a preventive, ameliorative or therapeutic effect against atopic dermatitis at the same level as that of steroid-based drugs such as dexamethasone. Therefore, the pharmaceutical composition is highly industrially applicable.

The specific examples described herein serve merely to illustrate preferred embodiments of the present invention and should not be construed as limiting the present invention. Those skilled in the art may be embodied in various modified or changed forms without departing from the spirit and scope of the present invention. Therefore, the scope of protection of the present invention should be defined by the attached claims, and various modifications and changes as described above are intended to fall within the scope of protection of the present invention.

[Accession Number]

Depository Authority: Korean Culture Center of Micro-organisms (International) having address of Yurim B/D 45, Hongjenae-2ga-go, Seodaemun-gu, SEOUL 03641 Republic of Korea.

Accession Number: KCCM12621P

Deposit Date: Nov. 1, 2019

5

---

The invention claimed is:

1. A composition containing a culture or a dried product of an isolated *Faecalibacterium prausnitzii* EB-FPDK11 strain (KCCM12621P) as an active ingredient, formulated with at least one pharmaceutically acceptable additive selected from the group consisting of wetting agents, sweetening agents, flavoring agents, binders, disintegrants, coating agents, lubricants, and preservatives.

2. The composition of claim 1, wherein the *Faecalibacterium prausnitzii* EB-FPDK11 strain has the 16s rRNA sequence set forth in SEQ ID NO: 1.

3. The composition of claim 1, wherein the *Faecalibacterium prausnitzii* EB-FPDK11 strain is live or pasteurized.

4. The composition of claim 1, further containing a vitamin or an immunosuppressant.

5. The composition of claim 4, wherein the immunosuppressant is selected from the group consisting of a calcineurin inhibitor selected from cyclosporine, tacrolimus, pimecrolimus and ISA (TX) 247;

rapamycin;

a Type IV phosphodiesterase (Type IV PDE) inhibitor;

mycophenolate mofetil; and dexamethasone.

6. The composition of claim 1, comprising as the active ingredient the *Faecalibacterium prausnitzii* EB-FPDK11 strain in an amount of $10^8$ to $10^{12}$ CFU, or pasteurized or inactivated *Faecalibacterium prausnitzii* EB-FPDK11 derived from the culture of the isolated *Faecalibacterium prausnitzii* EB-FPDK11 strain containing $10^8$ to $10^{12}$ CFU.

7. The composition of claim 1, wherein the composition is for use in the treatment or prevention of an atopic disease selected from the group consisting of asthma, atopic dermatitis, urticaria, allergic rhinitis, anaphylaxis, or food allergy.

8. A method for preventing or treating atopic disease in a subject in need thereof, comprising administering a composition comprising an isolated *Faecalibacterium prausnitzii* EB-FPDK11 strain (KCCM12621P) as an active ingredient to the subject.

9. The method of claim 8, wherein the *Faecalibacterium prausnitzii* EB-FPDK11 strain has the 16s rRNA sequence set forth in SEQ ID NO: 1.

10. The method of claim 8, wherein the *Faecalibacterium prausnitzii* EB-FPDK11 strain are is live or pasteurized.

11. The method of claim 8, wherein the composition further comprises a vitamin or an immunosuppressant.

12. The method of claim 11, wherein the immunosuppressant is selected from the group consisting of:

a calcineurin inhibitor selected from cyclosporine, tacrolimus, pimecrolimus and ISA (TX) 247;

rapamycin;

a Type IV phosphodiesterase (Type IV PDE) inhibitor;

mycophenolate mofetil; and dexamethasone.

13. The method of claim 8, wherein the composition comprises as the active ingredient the *Faecalibacterium prausnitzii* EB-FPDK11 strain in an amount of $10^8$ to $10^{12}$ CFU, or pasteurized or inactivated *Faecalibacterium prausnitzii* EB-FPDK11 derived from the culture of the isolated *Faecalibacterium prausnitzii* EB-FPDK11 strain containing $10^8$ to $10^{12}$ CFU.

14. The method of claim 8, wherein the atopic disease is asthma, atopic dermatitis, urticaria, allergic rhinitis, anaphylaxis, or food allergy.

15. The method of claim 8, wherein the composition is a pharmaceutical composition, a dietary supplement, a food, or a cosmetic composition.

16. A health functional food for preventing or ameliorating atopic disease containing a culture or dried product of an isolated *Faecalibacterium prausnitzii* EB-FPDK11 strain (KCCM12621P) as an active ingredient, formulated with at least one nutritionally acceptable additive selected from the group consisting of wetting agents, sweetening agents, flavoring agents, binders, disintegrants, coating agents, lubricants, and preservatives.

\* \* \* \* \*